US008067196B2

(12) United States Patent
Rosenberg et al.

(10) Patent No.: US 8,067,196 B2
(45) Date of Patent: Nov. 29, 2011

(54) 6-O SULFATED POLYSACCHARIDES AND METHODS OF PREPARATION THEREOF

(75) Inventors: Robert D. Rosenberg, Cambridge, MA (US); Lijuan Zhang, St. Charles, MO (US); David L. Beeler, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 942 days.

(21) Appl. No.: 10/473,180

(22) PCT Filed: Mar. 28, 2002

(86) PCT No.: PCT/US02/10172
§ 371 (c)(1),
(2), (4) Date: Mar. 25, 2004

(87) PCT Pub. No.: WO02/079258
PCT Pub. Date: Oct. 10, 2002

(65) Prior Publication Data
US 2004/0191870 A1    Sep. 30, 2004

Related U.S. Application Data

(60) Provisional application No. 60/279,523, filed on Mar. 28, 2001, provisional application No. 60/316,289, filed on Aug. 30, 2001.

(51) Int. Cl.
*C12P 11/00*    (2006.01)
*C12P 19/04*    (2006.01)
*C08B 37/00*    (2006.01)

(52) U.S. Cl. ........... 435/68.1; 536/54; 530/350; 530/395

(58) Field of Classification Search ........................ None
See application file for complete search history.

(56) References Cited

U.S. PATENT DOCUMENTS 5,834,282 A * 11/1998 Habuchi et al. ............... 435/193
5,955,347 A    9/1999 Lowe
6,365,365 B1 * 4/2002 Bistrup et al. ................. 435/15

OTHER PUBLICATIONS

Merriam-Webster Online Dictionary-definition of variant. Accessed May 14, 2008.*
Habuchi H, Tanaka M, Habuchi O, Yoshida K, Suzuki H, Ban K, Kimata K, "The Occurrence of Three Isoforms of Heparan Sulfate 6-O-sulfotransferase Havign Different Specificities for Hexuronic Acid Adjacent to the Targeted N-Sulfoglucosamine", The Journal of Biological Chemistry, 2000, 275(4): 2859-2868.*
Definition of derived from www.dictionary.com, pp. 1-5. Accessed Nov. 19, 2008.*
Do A-T, Smeds E, Spillman D, Kusche-Gullberg M, "Overexpression of Heparan Sulfate 6-O-Sulfotransferases in Human Embryonic Kidney 293 Cells Results in Increased N-Acetylglucosaminyl 6-O-sulfation," The Journal of Biological Chemistry, 2006, 281(9): 5348-5356.*
Rosenbeerg RD, Shworak NW, Liu J, Schwartz JJ, Zhang L, "Perspectives Series: Cell Adhesion in Vascular Biology," Journal of Clinical Investigation, 1997, 99(9): 2062-2070.*
Lansdon EB, Fisher AJ, Segel IH, "Human 3'-phosphoadenosine 5'-Phosphosulfate Synthetase (Isoform 1, Brain): Kinetic Properties of the Adenosine Triphosphate Sulfurylase and Adenosine 5'-Phosphosulfate Kinase Domains," Biochemistry, 2004, 43: 4356-5365.*
Perrimon N and Bernfield M, "Specificities of heparan sulphate proteoglycans in developmental processes," Nature, Apr. 13, 2000, 404: 725-728.*
Cook BN, Bhakta, Biegel T, Bowman KG, Armstron JI, Hemmerich S, Bertozzi CR, "Differential Carbohydrate Recognition of Two GIcNAc-6-sulfotransferase with Possible Roles in L-Selectin Ligand Biosynthesis," JACS, 2000, 122: 8612-8622.*
Chatterton Jon E. et al, Expression cloning of LDLB, a gene essential for normal Golgi function and assembly of the IdICp complex, Proc. Natl. Acad. Sci, USA, vol. 96, pp. 916-920, Feb. 1999, Cell Biology.
Habuchi, Hiroko et al., Molecular Characterization and Expression of Heparan-sulfate 6-Sulfotransferase, The Journal of Biological Chemistry, vol. 273, No. 15, Issue of Apr. 10, pp. 9208-9213, 1998, The American Society for Biochemistry and Molecular Biology, Inc.
Hwang Sherry Lih-Hwa, et al, Expression of Genes Introduced Into Cells by etoviralInfection Is More Efficient than that of Genes Introduced Into Cells by DNA Transfection, Journal of Virology, May 1984, pp. 417-424, vol. 50, No. 2 1984, American Society for Microbiology.
Kitamura Toshio et al., Efficient screening of retroviral cDNA expression libraries, Proc. Natl. Acad, Sci, USA, vol. 92, pp. 9146-9150, Sep. 1995, Biochemistry.
Kjellen Lena, et al. Proteoglycans: Structures and Interactions, Annu. Rev. Biochem. 1991, 60:443-75, Annual Reviews Inc.
Liu Jian et al., Heparan Sulfact d-Glucosaminyl 3-0-Sulfotransferase-3A Sulfates N-Unsubstituted Glucosamine Residues, The Journal of Biological Chemistry, vol. 274, No. 53, Issue of Dec. 31, pp. 38155-38162, 1999, The American Society for Biochemistry and Molecular Biology, Inc.
Merry Catherine L. R. et al., Highly Sensitive Sequencing of the Sulfated Domains of Heparan Sulfate, The Journal of Biological Chemistry, vol. 274. No. 26, Issue of Jun. 25, pp. 18455-18462, 1999, The American Society of Biochemistry and Molecular Biology, Inc.
Rayner John R. et al., A Simple and Efficient Procedure for Generating Stable Expression Libraries by cDNA Cloning in a Retroviral Vector, Molecular and Cellular Biology, vol. 14, No. 2, Feb. 1994 pp. 880-887, American Society for Microbiology.

(Continued)

*Primary Examiner* — Julie Ha
(74) *Attorney, Agent, or Firm* — Pearl Cohen Zedek Latzer, LLP; Mark S. Cohen

(57) ABSTRACT

Disclosed are methods of 6-O-sulfating glucosaminyl N-acetylglucosamine residues (GlcNAc) in a polysaccharide preparation and methods of converting anticoagulant-inactive heparan sulfate to anticoagulant-active heparan sulfate and substantially pure polysaccharide preparations may by such methods. Also disclosed is a mutant CHO cell which hyper-produces anticoagulant-active heparan sulfate. Methods for elucidating the sequence of activity of enzymes in a biosynthetic pathway are provided.

25 Claims, 8 Drawing Sheets

OTHER PUBLICATIONS

Shworak Nicholas W. et al., Multiple Isoforms of Heparan Sulfate D-Glucosaminyl 3-0-Sulfotransferase, The Journal of Biological Chemistry, vol. 274. No. 5, Issue of Feb. 19, pp. 5170-5184, 1999.

Wong Kenny K. et al. Engineering a Cell-Free Murein Biosynthetic Pahway: Combinatorial Enzymology in Drug Discovery, J. Am. Chem. Soc. 1998, 120, 13527-13528, American Chemical Society.

Wong Bryan Y. et al., High-Efficiency Identification of Genes by Functional Analysis from a Retroviral cDNA Expression Library, Journal of Virology, Sep. 1994, pp. 5523-5531, vol. 68. No. 9, American Society for Microbiology.

Zannettino Andrew C.W. et al. A Powerful New Technique for Isolating Genes Encoding Cell Surface Antigens Using Retroviral Expression Cloning, 1996 The American Association of Immunologists 156:611-620.

Zhang Lijuan et al. The Retinoic Acid and cAMP-Dependent Up-regulation of 3-0-Sulfotransferase-1 Leads to a Dramatic Augmentation of Anticoagulantly Active Heparan Sulfate Biosynthesis in F9 Embryonal Carcinoma Cells, The Journal of Biological Chemistry, vol. 273, No. 43 Issue of Oct. 23, pp. 27998-26003, 1998 The American Society for Biochemistry and Molecular Biology, Inc.

Zhang Lijuan et al., The Effect of Precursor structures on the Action of Glucosaminyl 3-0-Sulfotransferase-1 and the Biosynthesis of Anticoagulant Heparan Sulfate, The Journal of Biological Chemistry, vol. 276, No. 31 Issue of Aug. 3, pp. 28806-28813, 2001 The American Society of Biochemistry and Molecular Biology, Inc.

* cited by examiner

SEQUENCE LISTING

<160> NUMBER OF SEQ ID NOS: 20

<210> SEQ ID NO 1
<211> LENGTH: 1305
<212> TYPE: DNA
<213> ORGANISM: Homo sapiens

<400> SEQUENCE: 1

```
cgcggctcag taattgaagg cctgaaacgc ccatgtgcca ctgactagga ggcttccctg      60
ctgcggcact tcatgaccca gcggcgcgcg gcccagtgaa gccaccgtgg tgtccagcat     120
ggccgcgctg ctcctgggcg cggtgctgct ggtggcccag ccccagctag tgccttcccg     180
ccccgccgag ctaggccagc aggagcttct gcggaaagcg gggaccctcc aggatgacgt     240
ccgcgatggc gtggcccaaa cggctctgcc ccagcagttg ccgcagacca tcatcatcgg     300
cgtgcgcaag ggcggcacgc gcgcactgct ggagatgctc agcctgcacc ccgacgtggc     360
ggccgcggag aacgaggtcc acttcttcga ctgggaggag cattacagcc acggcttggg     420
ctggtacctc agccagatgc ccttctcctg gccacaccag ctcacagtgg agaagacccc     480
cgcgtatttc acgtcgccca aagtccctga gcgagtctac agcatgaacc cgtccatccg     540
gctgctgctc atcctgcgag acccgtcgga gcgcgtgcta tctgactaca cccaagtgtt     600
ctacaaccac atgcagaagc acaagcccta cccgtccatc gaggagttcc tggtgcgcga     660
tggcaggctc aatgtggact acaaggccct caaccgcagc ctctaccacg tgcacatgca     720
gaactggctg cgcttttttcc cgctgcgcca catccacatt gtggacggcg accgcctcat     780
cagggacccc ttccctgaga tccaaaaggt cgagaggttc ctaaagctgt cgccgcagat     840
caatgcttcg aacttctact ttaacaaaac caagggcttt tactgcctgc gggacagcgg     900
ccgggaccgc tgcttacatg agtccaaagg ccgggcgcac ccccaagtcg atcccaaact     960
actcaataaa ctgcacgaat attttcatga gccaaataag aagttcttcg agcttgttgg    1020
cagaacattt gactggcact gatttgcaat aagctaagct cagaaacttt cctactgtaa    1080
```

```
gttctggtgt acatctgagg ggaaaaagaa ttttaaaaaa gcatttaagg tataatttat   1140
ttgtaaaatc cataaagtac ttctgtacag tattagattc acaattgcca tatatactag   1200 ttatatttt  ctacttgtta aatggagggc attttgtatt gtttttcatg gttgttaaca   1260
ttgtgtaata tgtctctata tgaaggaact aaactatttc actga                    1305
```

<210> SEQ ID NO 2
<211> LENGTH: 307
<212> TYPE: PRT
<213> ORGANISM: Homo sapiens

<400> SEQUENCE: 2

```
Met Ala Ala Leu Leu Leu Gly Ala Val Leu Val Ala Gln Pro Gln
1               5                   10                  15

Leu Val Pro Ser Arg Pro Ala Glu Leu Gly Gln Gln Glu Leu Leu Arg
            20                  25                  30

Lys Ala Gly Thr Leu Gln Asp Asp Val Arg Asp Gly Val Ala Pro Asn
        35                  40                  45

Gly Ser Ala Gln Gln Leu Pro Gln Thr Ile Ile Gly Val Arg Lys
    50                  55                  60

Gly Gly Thr Arg Ala Leu Leu Glu Met Leu Ser Leu His Pro Asp Val
65                  70                  75                  80

Ala Ala Ala Glu Asn Glu Val His Phe Phe Asp Trp Glu Glu His Tyr
                85                  90                  95

Ser His Gly Leu Gly Trp Tyr Leu Ser Gln Met Pro Phe Ser Trp Pro
            100                 105                 110

His Gln Leu Thr Val Glu Lys Thr Pro Ala Tyr Phe Thr Ser Pro Lys
        115                 120                 125

Val Pro Glu Arg Val Tyr Ser Met Asn Pro Ser Ile Arg Leu Leu Leu
    130                 135                 140

Ile Leu Arg Asp Pro Ser Glu Arg Val Leu Ser Asp Tyr Thr Gln Val
145                 150                 155                 160

Phe Tyr Asn His Met Gln Lys His Asp Pro Tyr Pro Ser Ile Glu Glu
                165                 170                 175

Phe Leu Val Arg Asp Gly Arg Leu Asn Val Asp Tyr Lys Ala Leu Asn
            180                 185                 190

Arg Ser Leu Tyr His Val His Met Gln Asn Trp Leu Arg Phe Phe Pro
        195                 200                 205

Leu Arg His Ile His Ile Val Asp Gly Asp Arg Leu Ile Arg Asp Pro
    210                 215                 220

Phe Pro Glu Ile Gln Lys Val Glu Arg Phe Leu Lys Leu Ser Pro Gln
225                 230                 235                 240

Ile Asn Ala Ser Asn Phe Tyr Phe Asn Lys Thr Lys Gly Phe Tyr Cys
                245                 250                 255

Leu Arg Asp Ser Gly Arg Asp Arg Cys Leu His Glu Ser Lys Gly Arg
            260                 265                 270

Ala His Pro Gln Val Asp Pro Lys Leu Leu Asn Lys Leu His Glu Tyr
        275                 280                 285

Phe His Glu Pro Asn Lys Lys Phe Phe Glu Leu Val Gly Arg Thr Phe
    290                 295                 300

Asp Trp His
305
```

<210> SEQ ID NO 3
<211> LENGTH: 401
<212> TYPE: PRT

<213> ORGANISM: Homo sapiens

<400> SEQUENCE: 3

```
Met Val Glu Arg Ala Ser Lys Phe Val Leu Val Ala Gly Ser Val
1               5                  10                  15

Cys Phe Met Leu Ile Leu Tyr Gln Tyr Ala Gly Pro Gly Leu Ser Leu
            20                  25                  30

Gly Ala Pro Gly Gly Arg Ala Pro Pro Asp Asp Leu Tyr Leu Phe Pro
            35                  40                  45

Thr Pro Asp Pro His Tyr Glu Lys Lys Tyr Tyr Phe Pro Val Arg Glu
        50                  55                  60

Leu Glu Arg Ser Leu Arg Phe Asp Met Lys Gly Asp Asp Val Ile Val
65                  70                  75                  80

Phe Leu His Ile Gln Lys Thr Gly Gly Thr Thr Phe Gly Arg His Leu
                85                  90                  95

Val Gln Asn Val Arg Leu Glu Val Pro Cys Asp Cys Arg Pro Gly Gln
            100                 105                 110

Lys Lys Cys Thr Cys Tyr Arg Pro Asn Arg Arg Glu Thr Trp Leu Phe
            115                 120                 125

Ser Arg Phe Ser Thr Gly Trp Ser Cys Gly Leu His Ala Asp Trp Thr
130                 135                 140

Glu Leu Thr Asn Cys Val Pro Gly Val Leu Asp Arg Arg Asp Ser Ala
145                 150                 155                 160

Ala Leu Arg Thr Pro Arg Lys Phe Tyr Tyr Ile Thr Leu Leu Arg Asp
                165                 170                 175

Pro Val Ser Arg Tyr Leu Ser Glu Trp Arg His Val Gln Arg Gly Ala
            180                 185                 190

Thr Trp Lys Thr Ser Leu His Met Cys Asp Gly Arg Thr Pro Thr Pro
            195                 200                 205

Glu Glu Leu Pro Pro Cys Tyr Glu Gly Thr Asp Trp Ser Gly Cys Thr
210                 215                 220

Leu Gln Glu Phe Met Asp Cys Pro Tyr Asn Leu Ala Asn Asn Arg Gln
225                 230                 235                 240

Val Arg Met Leu Ala Asp Leu Ser Leu Val Gly Cys Tyr Asn Leu Ser
                245                 250                 255

Phe Ile Pro Glu Gly Lys Arg Ala Gln Leu Leu Leu Glu Ser Ala Lys
            260                 265                 270

Lys Asn Leu Arg Gly Met Ala Phe Phe Gly Leu Thr Glu Phe Gln Arg
            275                 280                 285

Lys Thr Gln Tyr Leu Phe Glu Arg Thr Phe Asn Leu Lys Phe Ile Arg
290                 295                 300

Pro Phe Met Gln Tyr Asn Ser Thr Arg Ala Gly Gly Val Glu Val Asp
305                 310                 315                 320

Glu Asp Thr Ile Phe Phe Ile Glu Glu Leu Asn Asp Leu Asp Met Gln
                325                 330                 335

Leu Tyr Asp Tyr Ala Lys Asp Leu Phe Gln Gln Arg Tyr Gln Tyr Lys
            340                 345                 350

Arg Gln Leu Glu Arg Arg Glu Gln Arg Leu Arg Ser Arg Glu Glu Arg
            355                 360                 365

Leu Leu His Arg Ala Lys Glu Ala Leu Pro Arg Glu Asp Ala Asp Glu
            370                 375                 380

Pro Gly Arg Val Pro Thr Glu Asp Tyr Met Ser His Ile Ile Glu Lys
385                 390                 395                 400

Trp
```

<210> SEQ ID NO 4
<211> LENGTH: 465
<212> TYPE: PRT
<213> ORGANISM: Homo sapiens

<400> SEQUENCE: 4

Met Ala Ser Val Gly Asn Met Asp Glu Lys Ser Asn Lys Leu Leu Leu
1               5                   10                  15

Ala Leu Val Met Leu Phe Leu Phe Ala Val Ile Val Leu Gln Tyr Val
            20                  25                  30

Cys Pro Gly Thr Glu Cys Gln Leu Leu Arg Leu Gln Ala Phe Ser Ser
        35                  40                  45

Pro Val Pro Asp Pro Tyr Arg Ser Glu Asp Glu Ser Ser Ala Arg Phe
    50                  55                  60

Val Pro Arg Tyr Asn Phe Thr Arg Gly Asp Leu Leu Arg Lys Val Asp
65                  70                  75                  80

Phe Asp Ile Lys Gly Asp Asp Leu Ile Val Phe Leu His Ile Gln Lys
                85                  90                  95

Thr Gly Gly Thr Thr Phe Gly Arg His Leu Val Arg Asn Ile Gln Leu
            100                 105                 110

Glu Gln Pro Cys Glu Cys Arg Val Gly Gln Lys Lys Cys Thr Cys His
        115                 120                 125

Arg Pro Gly Lys Arg Glu Thr Trp Leu Phe Ser Arg Phe Ser Thr Gly
    130                 135                 140

Trp Ser Cys Gly Leu His Ala Asp Trp Thr Glu Leu Thr Ser Cys Val
145                 150                 155                 160

Pro Ser Val Val Asp Gly Lys Arg Asp Ala Arg Leu Arg Pro Ser Arg
                165                 170                 175

Asn Phe His Tyr Ile Thr Ile Leu Arg Asp Pro Val Ser Arg Tyr Leu
            180                 185                 190

Ser Glu Trp Arg His Val Gln Arg Gly Ala Thr Trp Lys Ala Ser Leu
        195                 200                 205

His Val Cys Asp Gly Arg Pro Pro Thr Ser Glu Glu Leu Pro Ser Cys
    210                 215                 220

Tyr Thr Gly Asp Asp Trp Ser Gly Cys Pro Leu Lys Glu Phe Met Asp
225                 230                 235                 240

Cys Pro Tyr Asn Leu Ala Asn Asn Arg Gln Val Arg Met Leu Ser Asp
                245                 250                 255

Leu Thr Leu Val Gly Cys Tyr Asn Leu Ser Val Met Pro Glu Lys Gln
            260                 265                 270

Arg Asn Lys Val Leu Leu Glu Ser Ala Lys Ser Asn Leu Lys His Met
        275                 280                 285

Ala Phe Phe Gly Leu Thr Glu Phe Gln Arg Lys Thr Gln Tyr Leu Phe
    290                 295                 300

Glu Lys Thr Phe Asn Met Asn Phe Ile Ser Pro Phe Thr Gln Tyr Asn
305                 310                 315                 320

Thr Thr Arg Ala Ser Ser Val Glu Ile Asn Glu Glu Ile Gln Lys Arg
                325                 330                 335

Ile Glu Gly Leu Asn Phe Leu Asp Met Glu Leu Tyr Ser Tyr Ala Lys
            340                 345                 350

Asp Leu Phe Leu Gln Arg Tyr Gln Phe Met Arg Gln Lys Glu His Gln
        355                 360                 365

Glu Ala Arg Arg Lys Arg Gln Glu Gln Arg Asp Phe Leu Lys Gly Arg
    370                 375                 380

```
Leu Leu Gln Thr His Phe Gln Ser Gln Gly Gly Ser Gln Asn
385                 390                 395                 400

Pro Asn Gln Asn Gln Ser Gln Asn Pro Asn Pro Asn Ala Asn Gln Asn
            405                 410                 415

Leu Thr Gln Asn Leu Met Gln Asn Leu Thr Gln Ser Leu Ser Gln Lys
            420                 425                 430

Glu Asn Arg Glu Ser Pro Lys Gln Asn Ser Gly Lys Glu Gln Asn Asp
        435                 440                 445

Asn Thr Ser Asn Gly Thr Asn Asp Tyr Ile Gly Ser Val Glu Lys Trp
    450                 455                 460

Arg
465

<210> SEQ ID NO 5
<211> LENGTH: 504
<212> TYPE: PRT
<213> ORGANISM: Homo sapiens

<400> SEQUENCE: 5

Met Ala Ser Val Gly Asn Met Asp Glu Lys Ser Asn Lys Leu Leu Leu
1               5                   10                  15

Ala Leu Val Met Leu Phe Leu Phe Ala Val Ile Val Leu Gln Tyr Val
            20                  25                  30

Cys Pro Gly Thr Glu Cys Gln Leu Leu Arg Leu Gln Ala Phe Ser Ser
        35                  40                  45

Pro Val Pro Asp Pro Tyr Arg Ser Glu Asp Ser Ser Ala Arg Phe
    50                  55                  60

Val Pro Arg Tyr Asn Phe Thr Arg Gly Asp Leu Leu Arg Lys Val Asp
65                  70                  75                  80

Phe Asp Ile Lys Gly Asp Asp Leu Ile Val Phe Leu His Ile Gln Lys
                85                  90                  95

Thr Gly Gly Thr Thr Phe Gly Arg His Leu Val Arg Asn Ile Gln Leu
            100                 105                 110

Glu Gln Pro Cys Glu Cys Arg Val Gly Gln Lys Lys Cys Thr Cys His
        115                 120                 125

Arg Pro Gly Lys Arg Glu Thr Trp Leu Phe Ser Arg Phe Ser Thr Gly
    130                 135                 140

Trp Ser Cys Gly Leu His Ala Asp Trp Thr Glu Leu Thr Ser Cys Val
145                 150                 155                 160

Pro Ser Val Val Asp His Lys Arg Asp Ala Arg Leu Arg Pro Ser Arg
                165                 170                 175

Trp Arg Ile Phe Gln Ile Leu Asp Ala Ala Ser Lys Asp Lys Arg Gly
            180                 185                 190

Ser Ser Asn Thr Asn Ala Gly Ala Asn Ser Pro Val Ser His Lys Asp
        195                 200                 205

Pro Glu His Ile Arg Val Gly Asn Phe His Tyr Ile Thr Ile Leu Arg
    210                 215                 220

Asp Pro Val Ser Arg Tyr Leu Ser Glu Trp Arg His Val Gln Arg Gly
225                 230                 235                 240

Ala Thr Trp Lys Ala Ser Leu His Val Cys Asp Gly Arg Pro Pro Thr
                245                 250                 255

Ser Glu Glu Leu Pro Ser Cys Tyr Thr Gly Asp Asp Trp Ser Gly Cys
            260                 265                 270

Pro Leu Lys Glu Phe Met Asp Cys Pro Tyr Asn Leu Ala Asn Asn Arg
        275                 280                 285
```

```
Gln Val Arg Met Leu Ser Lys Leu Thr Leu Val Gly Cys Tyr Asn Leu
    290                 295                 300

Ser Val Met Pro Glu Lys Gln Arg Asn Lys Val Leu Leu Glu Ser Ala
305                 310                 315                 320

Lys Ser Asn Leu Lys His Met Ala Phe Phe Gly Leu Thr Glu Phe Gln
                325                 330                 335

Arg Lys Thr Gln Tyr Leu Phe Glu Lys Thr Phe Asn Met Asn Phe Ile
            340                 345                 350

Ser Pro Phe Thr Gln Tyr Asn Thr Thr Arg Ala Ser Ser Val Glu Ile
        355                 360                 365

Asn Glu Glu Ile Gln Lys Arg Ile Glu Gly Leu Asn Phe Leu Asp Met
370                 375                 380

Glu Leu Tyr Ser Tyr Ala Lys Asp Leu Phe Leu Gln Arg Tyr Gln Phe
385                 390                 395                 400

Met Arg Gln Lys Glu His Gln Glu Ala Arg Arg Lys Arg Gln Glu Gln
                405                 410                 415

Arg Lys Phe Leu Lys Gly Arg Leu Leu Gln Thr His Phe Gln Ser Gln
            420                 425                 430

Gly Gln Gly Gln Ser Gln Asn Pro Asn Gln Asn Gln Asn Pro
        435                 440                 445

Asn Pro Asn Ala Asn Gln Asn Leu Thr Gln Asn Leu Met Gln Asn Leu
450                 455                 460

Thr Gln Ser Leu Ser Gln Lys Glu Asn Arg Glu Ser Pro Lys Gln Asn
465                 470                 475                 480

Ser Gly Lys Glu Gln Asn Asp Asn Thr Ser Asn Gly Thr Asn Asp Tyr
                485                 490                 495

Ile Gly Ser Val Glu Lys Trp Arg
            500

<210> SEQ ID NO 6
<211> LENGTH: 471
<212> TYPE: PRT
<213> ORGANISM: Homo sapiens

<400> SEQUENCE: 6

Met Asp Glu Arg Phe Asn Lys Trp Leu Leu Thr Pro Val Leu Thr Leu
1               5                   10                  15

Leu Phe Val Val Ile Met Tyr Gln Tyr Val Ser Pro Ser Cys Thr Ser
                20                  25                  30

Ser Cys Thr Asn Phe Gly Glu Gln Pro Arg Glu Gly Glu Ala Gly Pro
            35                  40                  45

Pro Ala Val Pro Gly Pro Ala Arg Arg Ala Gln Ala Pro Pro Glu Glu
        50                  55                  60

Trp Glu Arg Arg Pro Gln Leu Pro Pro Pro Arg Gly Pro Pro Glu
65                  70                  75                  80

Gly Pro Arg Gly Ala Ala Ala Pro Glu Glu Asp Glu Glu Pro Gly
                85                  90                  95

Asp Pro Arg Glu Gly Glu Glu Glu Glu Asp Glu Pro Asp Pro
            100                 105                 110

Glu Ala Pro Glu Asn Gly Ser Leu Pro Arg Phe Val Pro Arg Phe Asn
        115                 120                 125

Phe Ser Leu Lys Ser Leu Thr Arg Phe Val Asp Phe Asn Ile Lys Gly
130                 135                 140

Arg Asp Val Ile Val Phe Leu His Ile Gln Lys Thr Gly Gly Thr Thr
145                 150                 155                 160
```

```
Phe Gly Arg His Leu Val Lys Asn Ile Arg Leu Glu Gln Pro Cys Ser
                165                 170                 175
Cys Lys Ala Gly Gln Lys Lys Cys Thr Cys His Arg Pro Gly Lys Lys
            180                 185                 190
Glu Thr Trp Leu Phe Ser Arg Phe Ser Thr Gly Trp Ser Cys Gly Leu
        195                 200                 205
His Ala Asp Trp Thr Glu Leu Thr Asn Cys Val Pro Ala Ile Met Glu
    210                 215                 220
Lys Lys Asp Cys Pro Arg Asn His Ser His Thr Arg Asn Phe Tyr Tyr
225                 230                 235                 240
Ile Thr Met Leu Arg Asp Pro Val Ser Arg Tyr Leu Ser Glu Trp Lys
                245                 250                 255
His Val Gln Arg Gly Ala Thr Trp Lys Thr Ser Leu His Met Cys Asp
            260                 265                 270
Gly Arg Ser Pro Thr Pro Asp Glu Leu Pro Thr Cys Tyr Pro Gly Asp
        275                 280                 285
Asp Trp Ser Gly Val Ser Leu Arg Glu Phe Met Asp Cys Thr Tyr Asn
    290                 295                 300
Leu Ala Asn Asn Arg Gln Val Arg Met Leu Ala Asp Ser Leu Ser Val
305                 310                 315                 320
Gly Cys Tyr Asn Leu Thr Phe Met Asn Glu Ser Glu Arg Asn Thr Ile
                325                 330                 335
Leu Leu Gln Ser Ala Lys Asn Asn Leu Lys Asn Met Ala Phe Phe Gly
            340                 345                 350
Leu Thr Glu Phe Gln Arg Lys Thr Gln Phe Leu Phe Glu Arg Thr Phe
        355                 360                 365
Asn Leu Lys Phe Ile Ser Pro Phe Thr Gln Phe Asn Ile Thr Arg Ala
    370                 375                 380
Ser Asn Val Glu Ile Asn Glu Gly Ala Arg Gln Arg Ile Glu Asp Leu
385                 390                 395                 400
Asn Phe Leu Asp Met Gln Leu Tyr Glu Tyr Ala Lys Asp Leu Phe Gln
                405                 410                 415
Gln Arg Tyr His His Thr Lys Gln Leu Glu His Gln Arg Asp Arg Gln
            420                 425                 430
Lys Arg Arg Glu Glu Arg Arg Leu Gln Arg Glu His Arg Asp His Gln
        435                 440                 445
Trp Pro Lys Glu Asp Gly Ala Ala Glu Gly Thr Val Thr Glu Asp Tyr
    450                 455                 460
Asn Ser Gln Val Val Arg Trp
465                 470

<210> SEQ ID NO 7
<211> LENGTH: 16
<212> TYPE: PRT
<213> ORGANISM: Artificial Sequence
<220> FEATURE:
<223> OTHER INFORMATION: Synthetic peptide that mimicks a heparin-
      binding domain of heparin interacting protein (HIP)

<400> SEQUENCE: 7

Cys Arg Pro Lys Ala Lys Ala Lys Ala Lys Ala Lys Asp Gln Thr Lys
1               5                   10                  15

<210> SEQ ID NO 8
<211> LENGTH: 40
<212> TYPE: DNA
<213> ORGANISM: Artificial Sequence
```

```
<220> FEATURE:
<223> OTHER INFORMATION: Sense primer with added BGI II site used for
      amplifying sequences coding for CHO 6-OST-1 derived from the human
      6-OST-1 cDNA sequence.

<400> SEQUENCE: 8
gcagatctgc aggaccatgg ttgagcgcgc cagcaagttc                               40

<210> SEQ ID NO 9
<211> LENGTH: 32
<212> TYPE: DNA
<213> ORGANISM: Artificial Sequence
<220> FEATURE:
<223> OTHER INFORMATION: Antisense primer with added Xba I site used for
      amplifying sequences coding for CHO 6-OST-1 derived from the human
      6-OST-1 cDNA sequence.

<400> SEQUENCE: 9
gctctagact accacttcta atgatgtggc tc                                      32

<210> SEQ ID NO 10
<211> LENGTH: 20
<212> TYPE: DNA
<213> ORGANISM: Artificial Sequence
<220> FEATURE:
<223> OTHER INFORMATION: Primer sequence used to amplify isoform
      specific regions with the human sequence for 6OST-1.

<400> SEQUENCE: 10
gcgtgcttca tgctcatcct                                                    20

<210> SEQ ID NO 11
<211> LENGTH: 19
<212> TYPE: DNA
<213> ORGANISM: Artificial Sequence
<220> FEATURE:
<223> OTHER INFORMATION: Primer sequence used to amplify isoform
      specific regions with the human sequence for 6OST-1.

<400> SEQUENCE: 11
gtgcgcccat cacacatgt                                                     19

<210> SEQ ID NO 12
<211> LENGTH: 20
<212> TYPE: DNA
<213> ORGANISM: Artificial Sequence
<220> FEATURE:
<223> OTHER INFORMATION: Primer sequence used to amplify isoform
      specific regions with the human sequence for 6OST-2.

<400> SEQUENCE: 12
ctgctgctgg ctttggtgat                                                    20

<210> SEQ ID NO 13
<211> LENGTH: 21
<212> TYPE: DNA
<213> ORGANISM: Artificial Sequence
<220> FEATURE:
<223> OTHER INFORMATION: Primer sequence used to amplify isoform
      specific regions with the human sequence for 6OST-2.

<400> SEQUENCE: 13
gcagaagaaa tgcacttgcc a                                                  21

<210> SEQ ID NO 14
<211> LENGTH: 20
<212> TYPE: DNA
<213> ORGANISM: Artificial Sequence
```

```
<220> FEATURE:
<223> OTHER INFORMATION: Primer sequence used to amplify isoform
      specific regions with the human sequence for 6OST-2.

<400> SEQUENCE: 14
gccgctatca ccttgtccct                                              20

<210> SEQ ID NO 15
<211> LENGTH: 19
<212> TYPE: DNA
<213> ORGANISM: Artificial Sequence
<220> FEATURE:
<223> OTHER INFORMATION: Primer sequence used to amplify isoform
      specific regions with the human sequence for 6OST-2.

<400> SEQUENCE: 15
tcattggtgc cattgctgg                                               19

<210> SEQ ID NO 16
<211> LENGTH: 19
<212> TYPE: DNA
<213> ORGANISM: Artificial Sequence
<220> FEATURE:
<223> OTHER INFORMATION: Primer sequence used to amplify isoform
      specific regions with the human sequence for 6OST-2.

<400> SEQUENCE: 16
tgagtgccag ttagcgcca                                               19

<210> SEQ ID NO 17
<211> LENGTH: 21
<212> TYPE: DNA
<213> ORGANISM: Artificial Sequence
<220> FEATURE:
<223> OTHER INFORMATION: Primer sequence used to amplify isoform
      specific regions with the human sequence for 6OST-3.

<400> SEQUENCE: 17
ccggtgctca ctttcctctt c                                            21

<210> SEQ ID NO 18
<211> LENGTH: 21
<212> TYPE: DNA
<213> ORGANISM: Artificial Sequence
<220> FEATURE:
<223> OTHER INFORMATION: Primer sequence used to amplify isoform
      specific regions with the human sequence for 6OST-3.

<400> SEQUENCE: 18
ttcaccctca aggacctgac c                                            21

<210> SEQ ID NO 19
<211> LENGTH: 20
<212> TYPE: DNA
<213> ORGANISM: Artificial Sequence
<220> FEATURE:
<223> OTHER INFORMATION: Primer sequence used to amplify isoform
      specific regions with the human sequence for 6OST-3.

<400> SEQUENCE: 19
gctctgcagc aggatggtgt                                              20

<210> SEQ ID NO 20
<211> LENGTH: 23
<212> TYPE: DNA
<213> ORGANISM: Artificial Sequence
<220> FEATURE:
<223> OTHER INFORMATION: Primer sequence used to amplify isoform
```

```
specific regions with the human sequence for 6OST-3.

<400> SEQUENCE: 20
gctggaagag atccttcgca tac                                            23
```

6-O SULFATED POLYSACCHARIDES AND METHODS OF PREPARATION THEREOF

This application is a National Stage Application of PCT International Application PCT/US02/10172, filed Mar. 28, 2002, which claims priority from U.S. provisional Application No. 60/279,523, filed Mar. 28, 2001, and U.S. provisional Application No. 60/316,289, filed Aug. 30, 2001, which are incorporated herein by reference.

RELATED APPLICATIONS

Benefit of priority is claimed to U.S. Provisional Application Serial No. 60/279,523, which was filed on Mar. 28, 2001, and U.S. Provisional Application Serial No. 60/316,289, which was filed on Aug. 30, 2001, the disclosures of which are herein incorporated by reference.

GOVERNMENT SUPPORT

Work described herein was supported by National Institutes of Health Grants 5-P01-HL41484, 5-R01-HL58479, and GM-50573. The Government has certain rights in the invention.

FIELD OF THE INVENTION

The present invention relates generally to the biosynthesis of glucosaminoglycans, and in particular to 6-O-sulfating polysaccharides.

BACKGROUND

Heparin/heparan sulfate (HS) is a linear polymer covalently attached to the protein cores of proteoglycans, which are abundant and ubiquitously expressed in almost all animal cells. HS is assembled by the action of a large family of enzymes that catalyze the following series of reactions: chain polymerization comprising the alternating addition of N-acetylglucosamine (GlcNAc) and glucuronic acid (GlcUA) residues; GlcNAc N-deacetylation and N-sulfation; glucuronic acid epimerization to L-iduronic acid (IdoUA); 2-O-sulfation of uronic acid residues; and 3-O- and 6-O-sulfation of glucosaminyl residues.

The interaction between HS and various proteins occur in highly sulfated regions of the HS. Furthermore, the specificity of any HS-protein interaction is largely dictated by arrangement of sulfates along the HS chain. For example, the pentasaccharide sequence, GlcNAc/NS6S-GlcUA-GlcNS3S±6S-IdoUA2S-GlcNS6S, represents the minimum sequence required for antithrombin (AT) binding, where the 3S (3-O-sulfate) and 6S (6-O-sulfate) groups constitute the most critical elements involved in the binding (12-16). The AT-HS complex has potent anticoagulant properties. Several enzymes involved in anticoagulant heparan sulfate ($HS^{act}$) biosynthesis have been purified and cloned. For example, glucosaminyl 3-O sulfotransferase (3-OST) and glucosaminyl 6-O-sulfotransferase (6-OST) proteins have been purified and cloned (17,18). Multiple isoforms of 6-OST and 3-OST proteins have been isolated and shown to have tissue-specific expression patterns and distinct substrate specificities.

Two different sulfated domains are present in HS, namely, the NS domain and NAc/NS domain (40,41). The NS domains consist of contiguous iduronosyl N-sulfoglucosamine units, while the NAc/NS domain consists of alternating N-acetylated and N-sulfated disaccharides. Acceptor specifcities of 6-OST-1, 6-OST-2, and 6-OST-3 using N-sulfated heparosan and desulfated re-N-sulfated heparin as substrate, indicated that the sulfation of position 6 of the N-sulfoglucosamine residues in the NS domain is catalyzed by 6-OST-1, 2A, 2B, and 3 and the sulfation of position 6 of the N-sulfoglucosamine residues in the NA/NS domain are catalyzed by 6-OST-2 and 6-OST-3 (2).

Tissue-specific and developmentally regulated expression of the HS biosynthetic enzymes and enzyme isoforms produce HS chains with specific sequences (1-3). This microheterogeneity enables HS to interact with a broad array of protein ligands that modulate a wide range of biological functions in development, differentiation, homeostasis, and bacterial/viral entry (reviewed in refs (4-11)). Synthetic polysaccharides which possess such specific sequences may be used to modulate such biological functions.

Heparin preparations, particularly preparations comprising $HS^{act}$, have been used clinically as anticoagulant therapeutics for the prevention and treatment of thrombotic disease. $HS^{act}$ preparations have also been used to maintain blood fluidity in extracoporeal or corporeal medical devices such as dialysis devices and stents, respectively.

SUMMARY OF THE INVENTION

In one aspect, the present invention features methods of transferring a sulfate on to the 6-O position of a GlcNAc sugar residue in a polysaccharide preparation, the method comprising the steps of (a) providing a polysaccharide preparation having GlcNAc sugar residues, and (b) contacting the polysaccharide preparation with 6-OST protein in the presence of a sulfate donor under conditions which permit the 6-OST protein to add a sulfate to the 6-O-position of a GlcNAc sugar residue. In preferred embodiments the sulfate donor is PAPS.

In some embodiments, the polysaccharide preparation comprises glucuronic acid (GlcUA) residues; GlcUA-GlcNAc sugar residues; disaccharides selected from the consisting of GlcUA/IdoUA-GlcNS, IdoUA2S-GlcNS, and GlcUA-GlcNS3S. In some preferred embodiments, the polysaccharide preparation includes the pentasaccharide sequence of the antithrombin binding motif, namely, GlcNAc/NS6S-GlcUA-GlcNS3S±6S-IdoUA2S-GlcNS6S.

In some embodiments, the polysaccharide preparation includes precursor saccharides for the antithrombin binding motif for example. GlcNAc/NS-GlcUA-GlcNS3S±6S-IdoUA2S-GlcNS6S, GlcNAc/NS6S-GlcUA-GlcNS3 S±-IdoUA2S-GlcNS6S, GlcNAc/NS6S-GlcUA-GlcNS3S±6S-IdoUA2S-GlcNS. Particularly preferred precursors include IdoA/GlcA-GlcNAc6S, IdoA/GlcA-GlcNS6S, and IdoA2S-GlcNS6S.

In some embodiments the 6-OST protein is a recombinant protein produced in an expression system such as baculovirus cells, bacteria cells, mammalian cells, or yeast cells. In some preferred embodiments the 6-OST is human 6-OST, however, 6-OST from other mammals may also be used. In particularly preferred embodiments, the 6-OST protein comprises a polypeptide selected from the group consisting of (a) human 6-OST-1 (SEQ ID NO. 3); (b) human 6-OST-2A (SEQ ID NO. 4); (c) human 6-OST-2B (SEQ ID NO. 5); (d) human 6-OST-3 (SEQ ID NO. 6); (e) an allelic or species variant of any of a-d; and (f) a functional fragment of any one of a-d.

In some embodiments, the sulfation reaction mixture comprising at least one chloride salt, and the pH is between 6.5 and 7.5 In preferred embodiments, the 6-OST is contacted with the polysaccharide preparation protein in the presence of a sulfate donor for at least 20 minutes. In other embodiments, the reaction proceeds overnight.

In another aspect, the present invention features method of enriching the portion of $HS^{act}$ present in a polysaccharide preparation comprising: (a) providing a 3-O-sulfated polysaccharide preparation; and (b) contacting the preparation with 6-OST protein in the presence of a sulfate donor under conditions, which permit the 6-OST protein to add a sulfate the 6-O-position of a GlcNAc sugar residue, wherein, step (b) occurs concurrent with or subsequent to step (a). In preferred embodiments, the sulfate donor is PAPS. In some embodiments, the polysaccharide preparation is derived from heparan; however, the polysaccharides may be derived from other sources of polysaccharides known in the art.

In some embodiments, the 3-O-sulfated polysaccharide preparation is derived from a cell that expresses 3-OST-1, in alternative embodiments, the 3-O-sulfated polysaccharide preparation is prepared by contacting $HS^{inact}$ with 3-OST-1 protein (SEQ ID NO 2), allelic or species variant, or functional fragments of 3-OST-1.

In preferred embodiments, the percentage of $HS^{act}$ present in the polysaccharide preparation following step (b) is greater than 50%. In particularly preferred embodiments, the percentage of $HS^{act}$ present in the polysaccharide preparation following step (b) is greater than 70%.

Preferred polysaccharide preparations for use in the methods of the invention comprise N-acetylglucosamine (GlcNAc) and glucuronic acid (GlcUA) residues. Particularly preferred polysaccharide preparations for use in the methods of the invention comprise GlcUA/IdoUA-GlcNS, GlcUA-GlcNAc, IdoUA2S-GlcNS, and GlcUA-GlcNS3S.

In another aspect, the present invention features, a mutant CHO cell ("hyper-producer") that produces between 28% and 50% $HS^{act}$. In preferred embodiment, the hyper-producer produces 50% $HS^{act}$ relative to total HS produced by the cell. The mutant CHO cell may be produced by a method comprising: (a) transforming a CHO cell with multiple copies of 3-OST-1, allelic or species variant or functional fragment thereof; (b) mutagenizing the cell obtained in step (a); (c) isolating a mutant cell from step (b) which fails to produce $HS^{act}$; and (d) transforming the cell obtained in step (c) with 6-OST. In particularly preferred embodiments, the 6-OST protein comprises a polypeptide selected from the group consisting of (a) human 6-OST-1 (SEQ ID NO. 3); (b) human 6-OST-2A (SEQ ID NO. 4); (c) human 6-OST-2B (SEQ ID NO. 5); (d) human 6-OST-3 (SEQ ID NO. 6); (e) an allelic or species variant of any of a-d; and (f) a functional fragment of any one of a-d.

In another aspect, the present invention features, a method of elucidating the sequence of components in a biosynthetic pathway comprising the steps of: (a) providing a target cell which expresses at least the upstream components of the biosynthetic pathway; (b) transforming the target cell with multiple copies of an isolated biosynthetic pathway downstream gene; (c) mutagenizing the transformed target cell; and (d) identifying transformed and mutagenized target cells that fail to express the phenotype characteristic of the biosynthetic pathway. In some embodiments, that method further comprises the step of (e) correcting the step (d) cells. In such embodiments, the correcting step may comprise inserting an upstream gene into the cells of step (d). The upstream gene may be a cDNA, genomic DNA, or a functional fragment thereof. In preferred embodiments, the cells of step (d) are transformed with a pool of preselected cDNAs for components of the biosynthetic pathway, for example, a cDNA library derived from a cell that expresses the characteristic non-mutant phenotype.

In some embodiments, the correcting step may comprise contacting the cells of step (d) with the gene product of an upstream gene. In alternative embodiments, the correcting step may comprise contacting the cells of step (d) with the mRNA, cDNA, genomic DNA, or a functional fragment thereof for the upstream gene.

In some embodiments, the method further comprises the step of isolating the cells from step (d), analyzing the cells of step (d), and/or isolating the upstream gene in the biosynthetic pathway.

In some embodiments, the mutagenesis step comprises a mutagenesis technique selected from the group consisting of chemical mutagenesis ion radiation, and ultraviolet radiation. The step of identifying the gene cDNA may comprise complementation analysis, Northern blot analysis, Southern blot analysis, and/or Western blot analysis. In preferred embodiments, upstream gene may be isolated using PCR or any other technique known in the art.

In another aspect, the present invention features methods of reducing thrombin activity in a medical device comprising the step of coating the medical device with any of the substantially pure preparations and/or preparations enriched for $HS^{act}$ disclosed herein. In preferred embodiments the medical device is an extracorporeal or intracorporeal device that contacts blood.

These and other objects, along with advantages and features of the invention disclosed herein, will be made more apparent from the description, drawings, and claims that follow.

DETAILED DESCRIPTION

Figure 1:
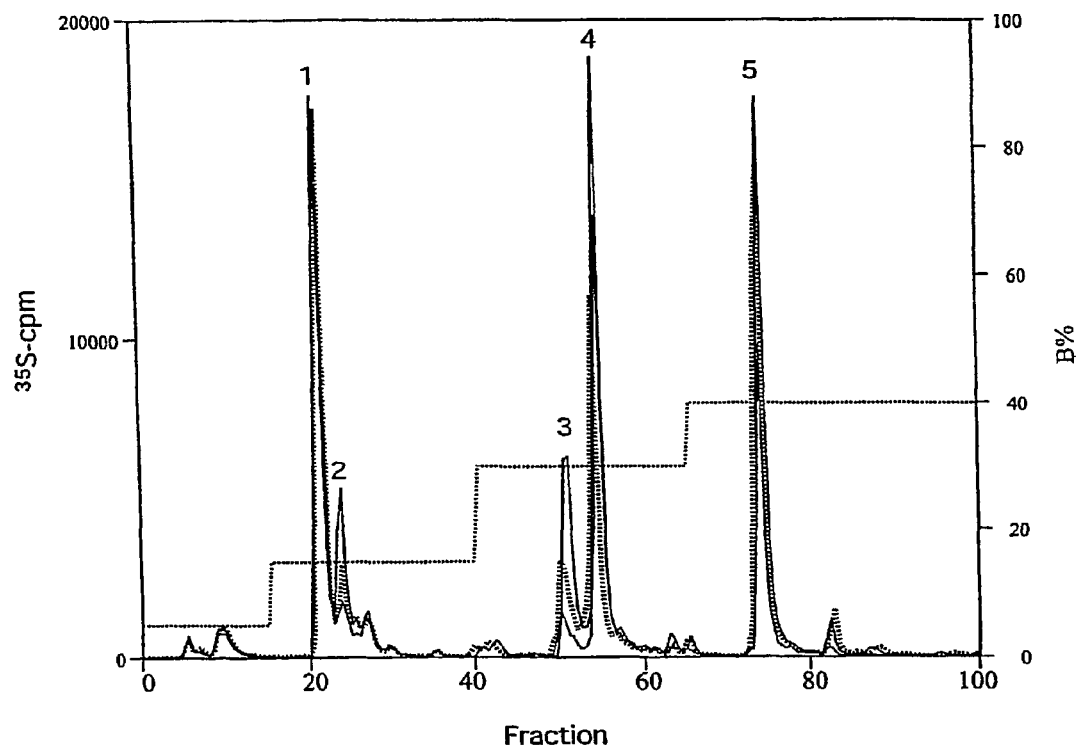
FIG. 1 depicts IPRP-HPLC of [$^{35}$S]sulfate metabolic labeled HS disaccharides. The IPRP-HPLC was performed as follows. [$^{35}$S]sulfate metabolically labeled HS from parental wild-type, mutant, and correctant were isolated and digested with a mixture of heparitinases. The resulting disaccharides were separated on a Bio-Gel P2 column and were then further resolved by IPRP-HPLC with appropriate internal standards. 1. ΔUA-GlcNS; 2. ΔUA-GlcNAc6S; 3. ΔUA-GlcNS6S; 4. ΔUA2S-GlcNS; 5. ΔUA2S-GlcNS6S. Blue tracer, mutant; red tracer, correctant; black broken tracer, wild-type. The broken line indicates the gradient of acetonitrile.

Before proceeding further with a detailed description of the currently preferred embodiments of the instant invention, an explanation of certain terms and phrases will be provided. Accordingly, it is understood that each of the terms set forth is defined herein at least as follows:

Anticoagulant heparan sulfate (HS$^{act}$). As used herein the term "anticoagulant heparan sulfate" or the abbreviation "HS$^{act}$" means a sulfated HS comprising the pentasaccharide binding site for antithrombin, namely, GlcNAc/NS6S-GlcUA-GlcNS3S±6S-IdoUA2S-GlcNS6S. HS$^{act}$ may be purified from a pool of polysaccharides by any means known in the art, for example, AT-affinity chromatography. The anticoagulant activity of a sample may be quantitated using the techniques disclosed herein, or alternatively using an assay known in the art, for example, the Coatest Heparin assay manufactured by Chromogenix, Milan, Italy.

Anticoagulant-inactive heparan sulfate (HS$^{inact}$) As used herein the term "anticoagulant-inactive heparan sulfate" or the abbreviation "HS$^{inact}$" means a sulfated HS lacking the pentasaccharide binding site for antithrombin, namely, GlcNAc/NS6S-GlcUA-GlcNS3S±6S-IdoUA2S-GlcNS6S. Anticoagulant-inactive heparan sulfate may also be identified and quantitated using the techniques disclosed herein or any assay known in the art, for example, the Coatest Heparin assay manufactured by Chromogenix, Milan, Italy.

Enriched. As used herein with regard to particular polysaccharide structures within a polysaccharide preparation, the term "enriched" means that the proportion of the polysaccharide structure in a polysaccharide preparation is statistically significantly greater than the proportion of the polysaccharide structure in naturally-occurring, untreated polysaccharide preparation. The polysaccharide preparations of the invention are enriched for 6-OST-1-sulfated polysaccharides or HS$^{act}$ approximately 10-100 fold. For example, whereas the percentage of 6-OST-sulfated polysaccharide in a typical, unenriched preparation is between 0%-3%, the percentage of 6-OST-sulfated polysaccharide in the enriched polysaccharide preparations of the invention is between approximately 5-9%. Likewise, whereas the percentage of HS$^{act}$ in a typical, produced by cells culture in vitro is between approximately 0-1%, the percentage of HS$^{act}$ in the enriched polysaccharide preparations of the invention derived from the hyper-producing mutant CHO cell of the invention is between approximately 28-50%.

Heparan sulfate. As used herein, the term "heparan sulfate" or the abbreviation "HS" means a polysaccharide made up of repeated disaccharide units D-glucuronic acid or L-iduronic acid linked to N-acetyl or N-sulfated D-glucosamine. The polysaccharide is modified to a variable extent by sulfation of the 2-O-position of GlcA and IdoA residues, and the 6-O- and 3-O-positions of GlcN residues and acetylation or de-acetylation of the nitrogen of GlcN residues. Therefore, this definition encompasses all of the glycosaminoglycan compounds variously referred to as heparan(s), heparan sulfate(s), heparin(s), heparin sulfate(s), heparitin(s), heparitin sulfate(s), heparanoid(s), heparosan(s). The heparan molecules may be pure glycosaminoglycans or can be linked to other molecules, including other polymers such as proteins, and lipids, or small molecules.

3-O-Sulfotransferases. As used herein, the term "3-O-Sulfotransferases" refers to the family of proteins that are responsible for the addition of sulfate groups at the 3-OH position of glucosamine in HS. These enzymes are present as several isoforms expressed from different genes at different levels in various tissues and cells. The 3-OSTs act to modify HS late in its biosynthesis (reviewed by Lindahl et al., 1998) and each isoform recognizes as substrate glucosamine residues in regions of the HS chain that have specific, but different, prior modifications, including epimerization and sulfation at other nearby positions (Liu et al., 1999). Thus, different 3-OSTs generate different potential protein-binding sites in HS.

3-OST-1. As used herein, the term "3-O-sulfotransferase-1" or the abbreviation "3-OST-1" refers to the particular isoform of the 6-O-Sulfotransferase family designated as "1". 3-OST-1 is described in detail in WO 99/22005, which is herein incorporated by reference in its entirety. As used herein 3-OST-1 may refer to the nucleic acid comprising the 3-OST-1 gene (SEQ. ID NO. 1) or the protein (SEQ. ID NO. 2). Whether the term is applied to nucleic acids or polypeptide, it is intended to embrace minimal sequences encoding functional fragments of 3-OST-1. In general, a functional fragment comprises the minimum segments required for transfer of a sulfate to the 3-O position of HS. Accordingly, a functional fragment may omit, for example, leader sequences that are present in full-length 3-OST-1. WO 99/22005 provides further guidance regarding which segments of full-length 3-OST-1 nucleic acids and polypeptides comprise functional fragments.

6-O-Sulfotransferases. As used herein, the term "6-O-Sulfotransferases" refers to members of the family of 6-OSTs are responsible for the addition of sulfate groups at the 6-OH position of glucosamine in HS. These enzymes are present as several isoforms expressed from different genes at different levels in various tissues and cells. As is the case with the 3-OSTs, the 6-OSTs act to modify HS late in its biosynthesis and each isoform recognizes as substrate glucosamine residues in regions of the HS chain that have specific, but different, prior modifications, including epimerization and sulfation at other nearby positions (Liu et al., 1999).

As used herein 6-OST may refer to nucleic acids or polypeptides comprising human 6-OST-1, -2A, -2B, and -3. Whether the term I applied to nucleic acids or polypeptide, it is intended to embrace allelic and species variants, as well as minimal segment(s) required for transfer of a sulfate to the 6-O position of an HS preparation and, in particular, GlcNAc residues of HS. Accordingly, a functional fragment may omit, for example, the transmembrane and/or leader sequences that are present in the full-length protein.

Substantially pure. As used herein with respect to polysaccharide preparations, the term "substantially pure" means a preparation which contains at least 60% (by dab weight) the polysaccharide of interest, exclusive of the weight of other intentionally included compounds. Preferably the preparation is at least 75%, more preferably at least 90%, and most preferably at least 99%, by dry weight the polysaccharide of interest, exclusive of the weight of other intentionally included compounds. Purity can be measured by any appropriate method, e.g., column chromatography, gel electrophoresis, amino acid compositional analysis or HPLC analysis. If a preparation intentionally includes two or more different polysaccharides of the invention, a "substantially pure" preparation means a preparation in which the total dry weight of the polysaccharide of the invention is at least 60% of the total dry weight, exclusive of the weight of other intentionally included compounds. Preferably, for such preparations containing two or more polysaccharides of the invention, the total weight of the polysaccharides of the invention should be at least 75%, more preferably at least 90%, and most preferably at least 99%, of the total dry weight of the preparation, exclusive of the weight of other intentionally included compounds. Thus, if the polysaccharides of the invention are mixed with one or more other compounds (e.g., diluents, detergents, excipients, salts, sugars, lipids) for purposes of administration, stability, storage, and the like, the weight of such other compounds is ignored in the calculation of the purity of the preparation. Furthermore, when the polysaccharide is a proteoglycan, the protein component of the proteoglycan is excluded for purposes of calculating purity.

Transformation. As used herein, transformation means any method of introducing exogenous a nucleic acid into a cell including, but not limited to, transformation, transfection, electroporation, microinjection, direct injection of naked nucleic acid, particle-mediated delivery, viral-mediated transduction or any other means of delivering a nucleic acid into a host cell which results in transient or stable expression of the nucleic acid or integration of the nucleic acid into the genome of the host cell or descendant thereof.

Variant. As used herein, "variant" DNA molecules are DNA molecules containing minor changes in a native 6-OST sequence, i.e., changes in which one or more nucleotides of a native 6-OST sequence is deleted, added, and/or substituted, preferably while substantially maintaining a 6-OST biological activity. Variant DNA molecules can be produced, for example, by standard DNA mutagenesis techniques or by chemically synthesizing the variant DNA molecule or a portion thereof. Such variants preferably do not change the reading frame of the protein-coding region of the nucleic acid and preferably encode a protein having no change, only a minor reduction, or an increase in 6-OST biological function. Amino-acid substitutions are preferably substitutions of single amino-acid residues. DNA insertions are preferably of about 1 to 10 contiguous nucleotides and deletions are preferably of about 1 to 30 contiguous nucleotides. Insertions and deletions are preferably insertions or deletions from an end of the protein-coding or non-coding sequence and are preferably made in adjacent base pairs. Substitutions, deletions, insertions or any combination thereof can be combined to arrive at a final construct. Preferably, variant nucleic acids according to the present invention are "silent" or "conservative" variants. "Silent" variants are variants of a native 6-OST sequence or a homolog thereof in which there has been a substitution of one or more base pairs but no change in the amino-acid sequence of the polypeptide encoded by the sequence. "Conservative" variants are variants of the native 6-OST sequence or a homolog thereof in which at least one codon in the protein-coding region of the gene has been changed, resulting in a conservative change in one or more amino acid residues of the polypeptide encoded by the nucleic-acid sequence, i.e., an amino acid substitution. In all instances, variants of the naturally-occurring 6-OST, as described above, must be tested for biological activity as described below. Specifically, they must have the ability to add a sulfate to the 6-OH position of a sugar residue in HS.

The present invention depends, in part on the discovery that (i) 6-OST is limiting enzyme in the $HS^{act}$ biosynthetic pathway when 3-OST-1 is non-limiting; (ii) 6-OST can add 6-O-sulfate to GlcNAc residues, including the critical 6-O-sulfate in the antithrombin binding motif of HS; and (iii) both 3-O- or 6-O-sulfation may be the final step in $HS^{act}$ biosynthesis. Thus, the present invention provides methods of synthesizing oligosaccharides comprising GlcNAc6S, preparations enriched for $HS^{act}$, and methods of making such preparations using 6-OST.

Methods of 6-O-Sulfating Polysaccharides

In one aspect, the present invention provides methods for 6-O-sulfating saccharide residues within a preparation of polysaccharides in which the polysaccharides includes a GlcNAc sugar residue. These methods comprise contacting a polysaccharide preparation with 6-OST protein in the presence of a sulfate donor under conditions which permit the 6-OST to convert the GlcNAc sugar residue to GlcNAc6S. In particularly preferred embodiments, the 6-OST protein comprises a polypeptide selected from the group consisting of (a) human 6-OST-1 (SEQ ID NO. 3); (b) human 6-OST-2A (SEQ ID NO. 4); (c) human 6-OST-2B (SEQ ID NO. 5); (d) human 6-OST-3 (SEQ ID NO. 6); (e) an allelic or species variant of any of a-d; and (f) a functional fragment of any one of a-d. In preferred embodiments, the sulfate donor is 3'-phospho-adenosine 5'-phosphosulfate (PAPS).

In another aspect, the present invention provides methods of producing $HS^{act}$ by contacting a 3-O-sulfated polysaccharide preparation with 6-OST protein. These methods are based upon the discovery that 6-O-sulfation can occur after 3-O-sulfation in $HS^{act}$ biosynthesis. In particular embodiments, a GlcNAc sugar residue which comprises a part of an $HS^{act}$ precursor sequence is 6-O-sulfated. In some embodiments, the target polysaccharide comprises part of an $HS^{act}$ precursor sequence, for example, IdoA/GlcA-GlcNAc6S, IdoA/GlcA-GlcNS6S, and IdoA2S-GlcNS6S. In some preferred embodiments, the target polysaccharide is 3-O-sulfated prior to or concurrently with 6-O-sulfation.

In another aspect, the present invention also provides for means of enriching the AT-binding fraction of a heparan sulfate pool (i.e., increasing the portion of $HS^{act}$) by contacting a polysaccharide preparation with 6-OST protein in the presence of a sulfate donor under conditions which permit the 6-OST to convert $HS^{inact}$ to $HS^{act}$. In preferred embodiments, the sulfate donor is 3'-phospho-adenosine 5'-phosphosulfate (PAPS). Conversion of the $HS^{act}$ precursor pool to $HS^{act}$ using the methods of the invention is particularly useful in the production of anticoagulant heparan sulfate products which have clinical applications as therapeutics, for example, as an agent to treat or prevent thrombotic disease. Anticoagulant heparan sulfate products may alternatively be used as agents to maintain blood flow in medical devices, for example, dialysis machines. In general, the preparations enriched for $HS^{act}$ disclosed herein may be use in any application in which anticoagulant HS is employed.

In yet another aspect, the present invention provides a recombinant cell line that expresses enhanced levels of $HS^{act}$. In vitro cell cultures produce between 0%-1% $HS^{act}$. However; the corrected mutant ("correctant or hyper-producer") created by transforming CHO cells multiple copies of 3-OST-1, followed mutigenization of the resultant transformant and transformation with 6-OST-1 has been shown to express between 28%-50% $HS^{act}$. This represents a significant improvement over the percentage of $HS^{act}$ produced by any cell line known to applicants at the time of filing.

The 6-O-sulfated preparations and the $HS^{act}$ produced by the methods of the invention are useful as therapeutic agents to treat and/or prevent any condition improved by administration of an anticoagulant, for example, thrombotic disease. These compositions may also be used to coat the surfaces of extracorporeal medical devices (e.g., dialysis tubing) or intracorporeal devices (e.g., transplants, stents or other prosthetic implants) to reduce blood clotting on those surfaces.

Practice of the invention will be still more fully understood from the examples, which are presented herein for illustration only and shall not be construed as limiting the invention in any way.

Example 1

6-O-sulfation of HS In Vitro

6-O-sulfation of glucosaminylglyans in vitro may be accomplished in any manner known in the art. As a skilled artisan would recognize, a 6-O-sulfation reaction requires a 6-OST protein, or functional fragment thereof, a target polysaccharide, a sulfate donor (preferably PAPS), and a pH in the range of 6.5-7.5 (preferably a pH of about 7.0). Thus, in a preferred procedure, the reaction mixture contains 50 mM MES (pH 7.0), 1% (w/v) Triton X-100, 5 mM $MnCl_2$, 5 mM $MgCl_2$, 2.5 mM $CaCl_2$, 0.075 mg/ml protamine chloride, 1.5 mg/ml BSA, either metabolically labeled [$^{35}$S]HS or non-radioactive HS chains, cold PAPS (0.5 mM) or [$^{35}$S]PAPS (25 µM, 2×10$^7$ cpm), and 70 ng of purified baculovirus-expressed human 6-OST-1 in a final volume of 50 µl. The mixtures may be incubated either 20 minutes or overnight at 37° C., and 200 µg of chondroitin sulfate C added. HS chains are purified by phenol/chloroform extraction and anion exchange chromatography on 0.25-ml columns of DEAE-Sephacel packed in 1 ml syringes (20). After ethanol precipitation, the pellets are washed with 75% ethanol, dried briefly under vacuum, and dissolved in water for further analysis.

Example 2

6-OST Generate $HS^{act}$ In Vitro

To explain the difference between 6-OST substrate specificity observed in vivo and previously reported specifcities, 6-OST-1 was expressed and purified in bacteria and baculovirus. The purified proteins were used to sulfate HS$^{35}$S derived from the precursor mutant and wild-type CHO cells. Specifically, precursor mutant HS chains were treated with baculovirus expressed, 3-OST-1 protein, 6-OST-1 protein, or both proteins in the presence of cold PAPS. $HS^{act}$ was isolated by AT-affinity purification and the percentage of $HS^{act}$ was quantitated. The results are shown below in Table 1. As Table 1 shows, the yield of $HS^{act}$ resulting from 6-OST-1 treatment of precursor mutant HS chain (51%) was similar to that of the CHO wild-type (64%) even though 6-O-sulfation is severely decreased in the precursor mutant (FIG. 1).

TABLE 1

| | Percentage of [S$^{35}$]HS$^{act}$ | | | |
|---|---|---|---|---|
| | Control | 3-OST-1 | 6-OST-1 | 3-OST-1 and 6-OST-1 |
| Wild-type CHO | 26% | 40% | 64% | 70% |
| Precursor Mutant | 7% | 12% | 51% | 64% |

Example 3

Figure 2:
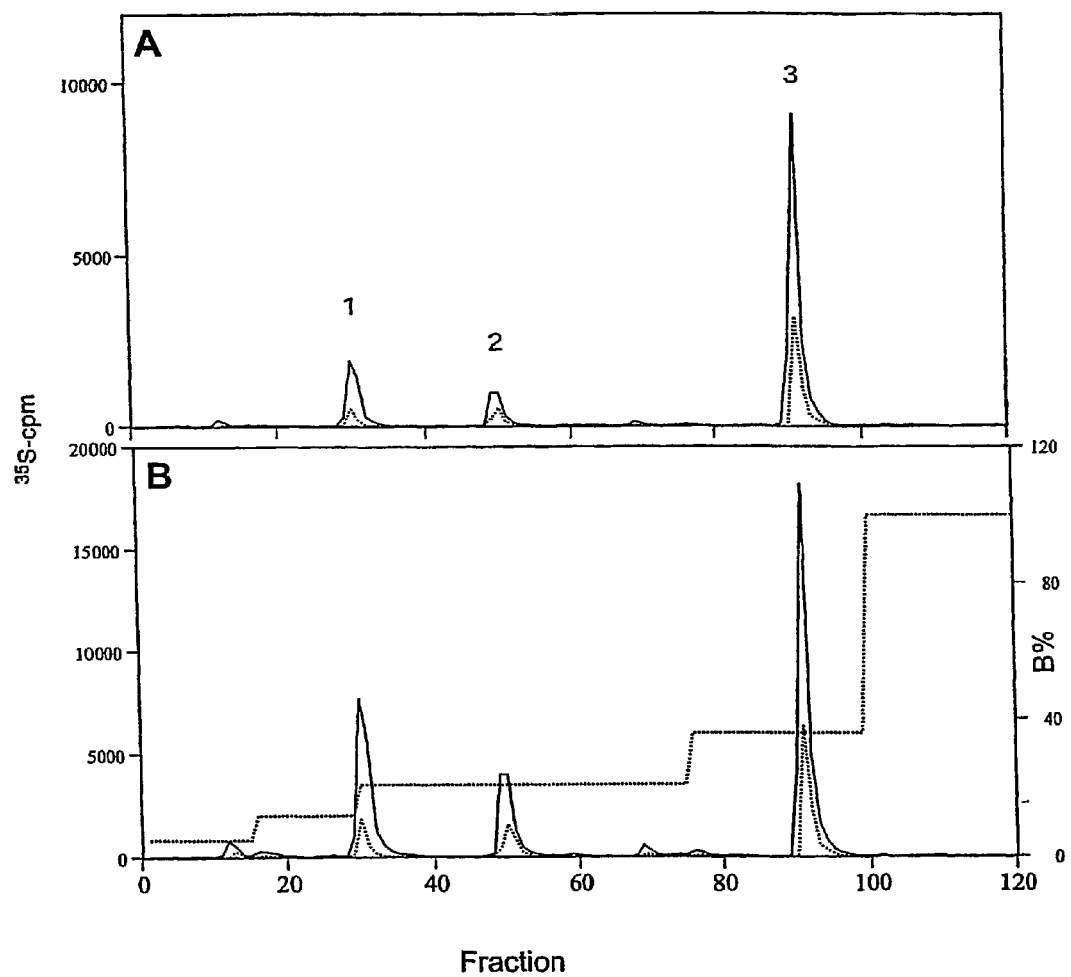
FIG. 2 depicts IPRP-HPLC of 6-OST-1 and [$^{35}$S]PAPS-labeled HS disaccharides. The IPRP-HPLC was performed as follows. Cold HS from 3-OST-1 expressing CHO wild-type and precursor mutant were in vitro labeled with purified baculovirus expressed 6-OST-1 in the presence [$^{35}$S]PAPS for 20 min. (A) or overnight (B). HS[$^{35}$S] was isolated and digested with a mixture of heparitinases. The resulting disaccharides were separated on a Bio-Gel P2 column and further resolved by IPRP-HPLC with internal standards. 1. ΔUA-GlcNAc6S; 2. ΔUA-GlcNS6S; 3. ΔUA2S-GlcNS6S. Solid tracer, mutant; broken tracer, wild-type. The broken line indicates the gradient of acetonitrile.

6-OST-1 Sulfation Generates Three Kinds of 6-O-Containing Disaccharides In Vitro To localize where 6-OST-1 adds 6S residues along the HS chains, equal amounts of HS from 3-OST-1 expressing wild-type and precursor mutant were in vitro labeled with purified baculovirus expressed 6-OST-1 in the presence of [$^{35}$S]PAPS either for 20 minutes or overnight. Only ~⅓ as much radioactivity was incorporated into the HS derived from 3-OST-1 expressing CHO cells as compared to the HS derived from the precursor mutant cells. [S$^{35}$]HS was isolated and digested with a mixture of heparitinases. The resulting disaccharides (accounting for ~94% of [$^{35}$S] counts) were separated on a Bio-Gel P2 column and further resolved by IPRP-HPLC with appropriate internal standards (FIG. 2, mutant, solid tracer; wild-type, broken tracer). As FIG. 2 shows, 6-OST-1 not only added a 6S group on GlcNS, but 6-OST-1 also 6S group on GlcNAc residues in both the 3-OST-1 expressing CHO HS and precursor mutant HS.

As summarized below in Table 2, more ΔUA-GlcNAc6$^{35}$S and ΔUA-GlcNS6$^{35}$S disaccharides were observed from reactions run overnight than after just 20 minutes. 6-O-sulfate incorporation was 10 times higher from incubation with baculovirus expressed 6-OST-1 than bacteria expressed 6-OST-1. However, overnight labeling using bacterial 6-OST-1 generated three 6-O-sulfated disaccharides in the following proportions: ΔUA-GlcNAc6$^{35}$S (25%), ΔUA-GlcNS6$^{35}$S (20%), and ΔUA2S-GlcNS6$^{35}$S (55%). This ratio of 6-O-sulfated disaccharides is comparable to the ratio observed in baculovirus 6-OST-1 overnight labeled disaccharides (FIG. 2, panel B).

TABLE 2

|  | Overnight Incubation | 20 Minute Incubation |
|---|---|---|
| ΔUA-GlcNAc6$^{35}$S | 29% | 18% |
| ΔUA-GlcNS6$^{35}$S | 18% | 12% |
| ΔUA2S-GlcNS6$^{35}$S | 53% | 70% |

Example 4

Contribution of 6-OST in Generation of HS$^{act}$ Oligosaccharides

Figure 3:
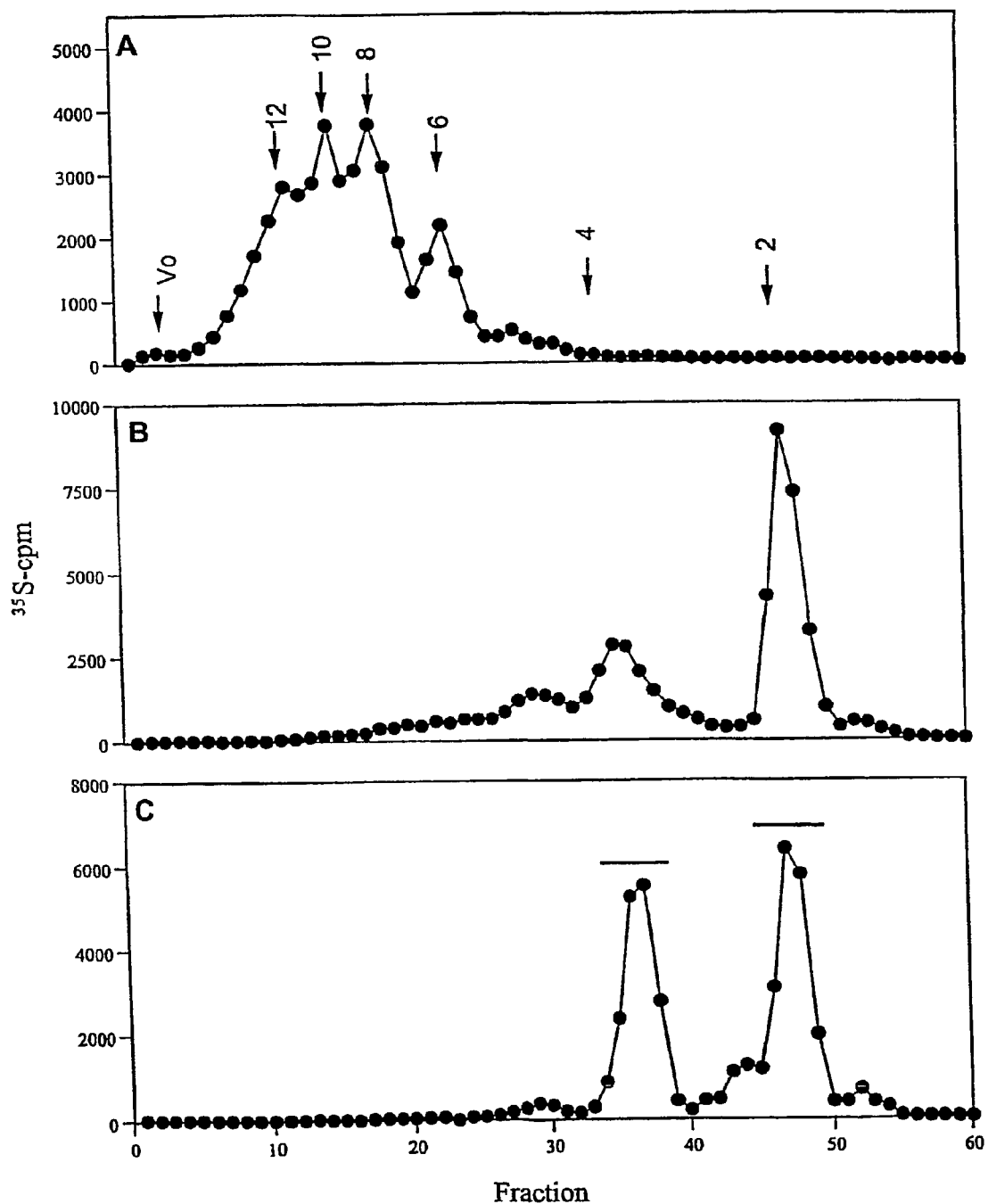
FIG. 3 depicts Bio-Gel P6 fractionation of digested HS. The Bio-Gel P6 fractionation was performed as follows. 6-O-[$^{35}$S]sulfate tagged [$^{3}$H]HS from mutant were digested with 1 mU heparitinase I for 1 hour. $HS^{act}$ oligosaccharides were obtained by AT-affinity chromatography. $HS^{act}$ oligosaccharides were then treated with low pH nitrous acid and then NABH$_4$ reduced, or treated with heparitinase I, II, and heparinase were analyzed by Bio-Gel P6 chromatography. The fractions indicated were pooled for further analysis. A, 6-O-[$^{35}$S]sulfate tagged mutant $HS^{act}$ oligosaccharides; B, 6-O-[$^{35}$S]sulfate tagged mutant $HS^{act}$ oligosaccharides treated with low pH nitrous acid and NaBH$_4$; C, 6-O-[$^{35}$S]sulfate tagged mutant $HS^{act}$ oligosaccharides digested with heparitinases. n=the number of monosaccharide units in each peak.
Figure 4:
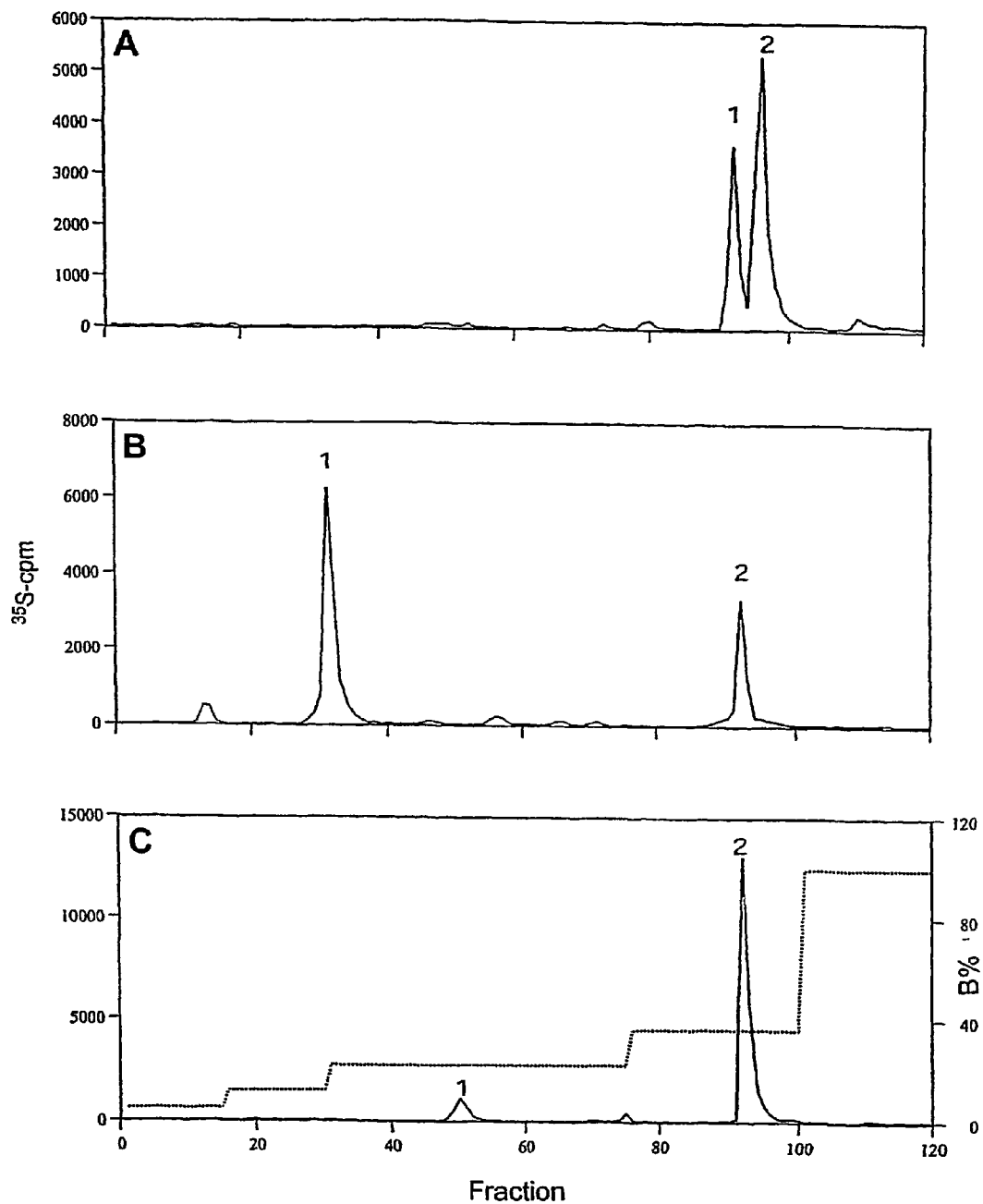
FIG. 4 depicts IPRP-HPLC of 6-O-sulfate tagged HS$^{act}$ di- and tetrasaccharides. The IPRP-HPLC was performed as follows. In vitro 6-O-sulfated and AT-affinity purified [$^3$H]HS$^{act}$ oligosaccharides were digested with a mixture of heparitinases. The resulting di- and tetrasaccharides were separated on a Bio-Gel P6 column (FIG. 3C). (A), tetrasaccharides collected from FIG. 3C, peak 1: ΔUA-GlcNAc6$^{35}$S-GlcUA-GlcNS3S, peak 2: ΔUA-GlcNAc6$^{35}$S-GlcUA-GlcNS3S6$^{35}$S; (B), disaccharides of the digested tetrasaccharides in the presence of HIP peptide; peak 1: ΔUA-GlcNAc6$^{35}$S, peak 2: ΔUA-GlcNS3S6$^{35}$S; (C), disaccharides collected from FIG. 3C, peak 1: ΔUA-GlcNS6$^{35}$S, peak 2: ΔUA2S-GlcNS6$^{35}$S. The broken line indicates the gradient of acetonitrile.
Figure 8:
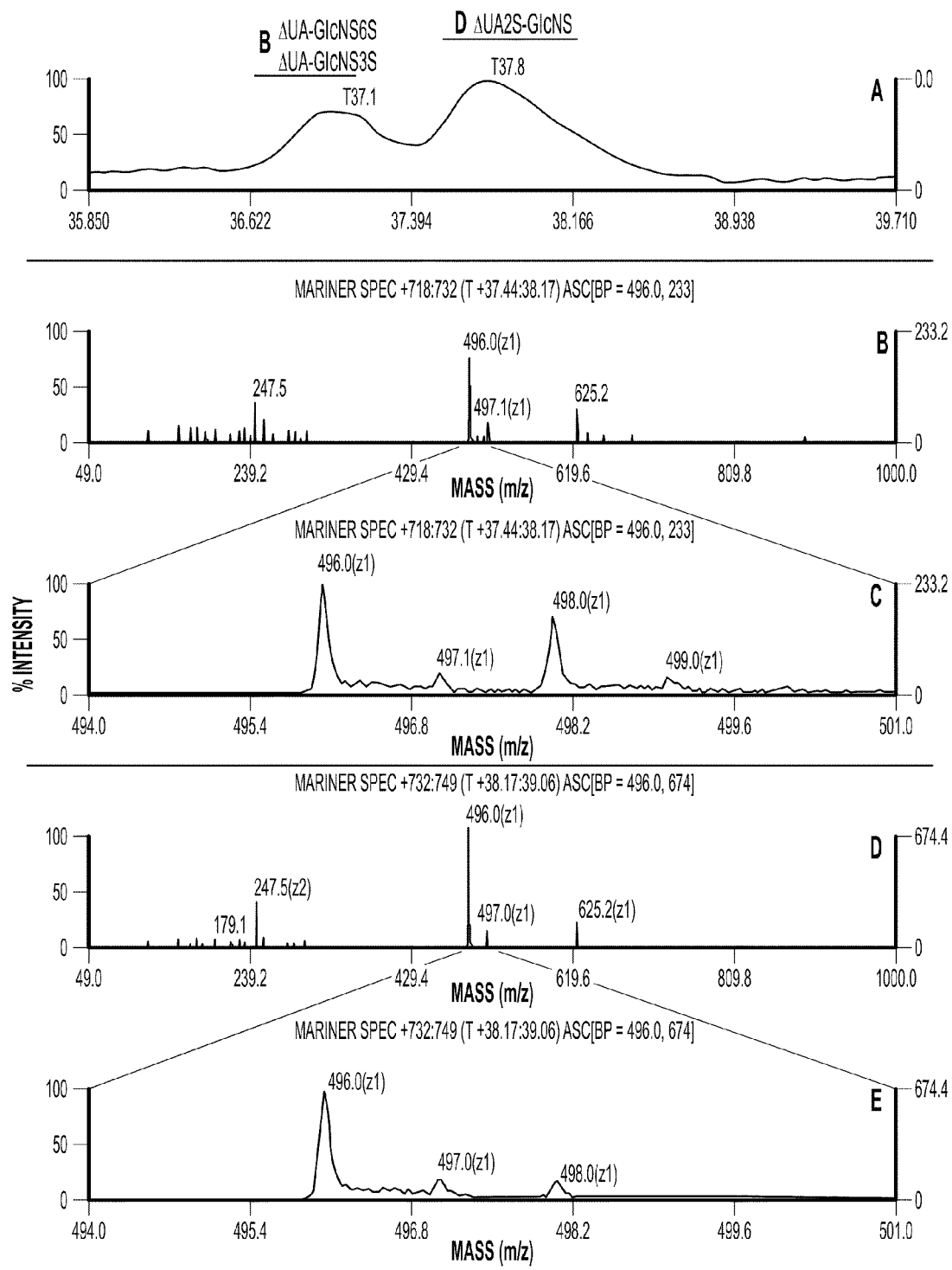
FIG. 8 depicts ΔUA-GlcNS3 S disaccharide structure as determination by capillary IPRP-HPLC coupled with mass spectrometry. The IPRP-HPLC-MS analysis was performed as follows. Cold HS chain from wild-type CHO cells were labeled with 3-OST-1 plus PAP$^{34}$S. Purified HS was digested with a combination of 1 mU of each heparitinase I, heparitinase II, heparitinase IV, and heparinase in the presence of 0.5 mg/ml heparin/heparan sulfate interacting protein (HIP) peptide. 0.5 µg of digested HS was injected into capillary IPRP-HPLC coupled with MS. Panel A, UV tracer of capillary IPRP-HPLC from 35.85 to 39.71 min., peak B contains both ΔUA-GlcNS6S and ΔUA-GlcNS3 S, and peak D contains ΔUA2S-GlcNS; panel B, negative polarity MS spectra from 37.44 to 38.17 min.; which equals UV peak from 36.64 to 37.37 min.; panel C, amplification of m/z 494.0 to 501.0 region from panel B; panel D, negative polarity MS spectra from 38.17 to 39.06 min.; which equals UV peak from 37.37 to 38.26 min.; panel E, amplification of m/z 494.0 to 501.0 region from panel D.

To further locate the 6-O-sulfate addition in AT-binding HS$^{act}$ oligosaccharides, cold mutant HS chains were treated with purified Baculovirus expressed 6-OST-1 with [$^{35}$S] PAPS overnight. After heparitinase I digestion, HS$^{act}$ oligosaccharides were affinity purified (7% of 6-O-[$^{35}$S]sulfate-labeled HS$^{total}$). The HS$^{act}$ oligosaccharides were then treated with low pH nitrous acid that cleaves N-sulfated residues, and a combination of heparitinases that cleaves 3-O-sulfate containing sugar into tetrasaccharides and all other sugars into disaccharides. Treated and untreated HS$^{act}$ oligosaccharides were run on Bio Gel P6 columns (FIG. 3). Di- and tetrasaccharides were collected from enzyme and low pH nitrous treated samples as indicated. The tetrasaccharides resistant to a combination of heparitinases I, II, and heparinase digestion represented the 3-O-sulfate containing tetrasaccharides as reported earlier (20,33). The presence of similar amounts of tetrasaccharides from both nitrous and enzyme degradation suggests the 3-O-containing tetrasaccharides have the structures, UA±2S-GlcNAc6$^{35}$ S-GlcUA-GlcNS3 S±6$^{35}$S. To prove this, the tetrasaccharides (FIG. 4A) collected from enzyme digestion (FIG. 3C) were further digested into disaccharides (FIG. 4B) with heparitinase I in the presence of HIP peptide (the same method as shown in FIG. 8). IPRP-HPLC profiles of 6-O-sulfate tagged HS$^{act}$ di- and tetrasaccharides from FIG. 3C were shown in FIG. 8. Table 3 summarizes the 6-O-[$^{35}$S]sulfate-labeled disaccharide compositions calculated based on the HPLC data (FIG. 4).

TABLE 3

| Percentage of [S$^{35}$]HS$^{act}$ | | | | |
|---|---|---|---|---|
|  | Control | 3-OST-1 | 6-OST-1 | 3-OST-1 and 6-OST-1 |
| Wild-type CHO | 26% | 40% | 64% | 70% |
| Precursor Mutant | 7% | 12% | 51% | 64% |

In HS$^{act}$ oligosaccharides, 6-OST adds 6-O-sulfates not only at GlcUA/IdoUA-GlcNS, GlcUA-GlcNAc, and IdoUA2S-GlcNS, but also at GlcUA-GlcNS3S. These results show that 6-OST is the enzyme that not only puts the critical 6-O-sulfate group in HS$^{act}$ oligosaccharides, but also other 6-O-sulfate groups in HS$^{act}$ oligosaccharides as well. 3-OST-1 and 6-OST are therefore the critical enzymes for the generation of HS$^{act}$.

3-OST-1, usually existing in limited amounts, acts upon HS$^{act}$ precursor to produce HS$^{act}$ and upon HS$^{inact}$ precursor to produce 3-O-sulfated HS$^{inact}$ (17,19). When 3-OST-1 is no longer limiting, the capacity for HS$^{act}$ generation is determined by the abundance of HS$^{act}$ precursors (20). Since in vitro 3-O-sulfation can transform HS$^{inact}$ into HS$^{act}$, it was previously believed that 3-O-sulfation is the final modification step during biosynthesis of HS$^{act}$. Surprisingly, in vitro 6-O-sulfation was also shown to transform 3-O-sulfate containing HS$^{inact}$ into HS$^{act}$. Thus, the present disclosure provides methods of enriching a polysaccharide preparation of HS$^{act}$ by contacting a HS$^{inact}$ with 6-O-sulfate protein and a sulfate donor under conditions which permit 6-OST-1 to sulfate a GlcNAc sugar residue.

Example 5

6-OST-1 Corrected Mutant Makes HS, 50% of which is HS$^{act}$

Figure 5:
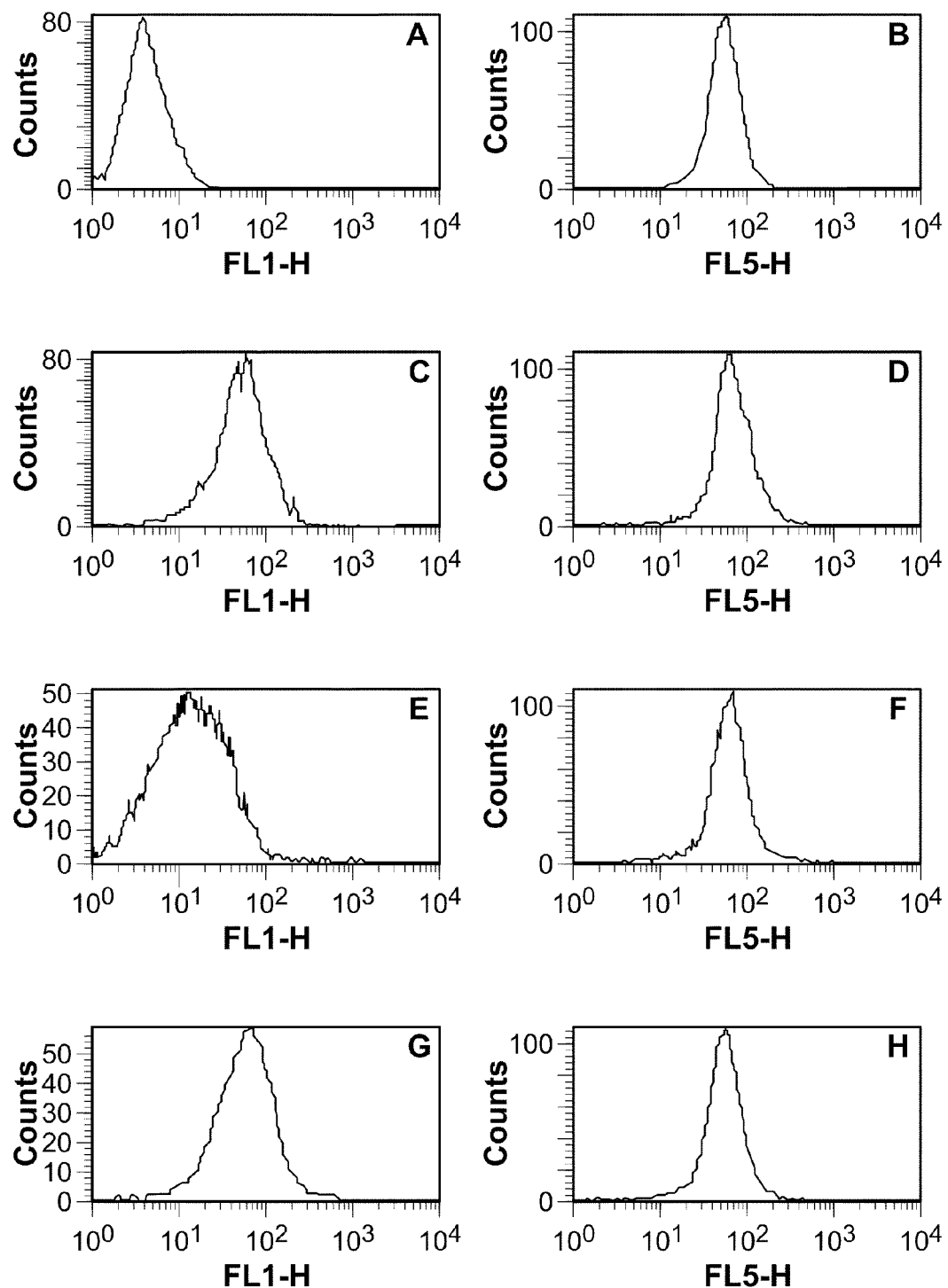
FIG. 5 depicts dual-color fluorescence flow cytometric analysis of AT (A, C, E, and G) and FGF-2 (B. D, F, and H) binding to wild-type, mutant, and 6-OST-1 correctant. CHO wild-type (A and B); wild-type CHO cell clone with 3 copies of 3-OST-1, (C and D), mutant cell clone with 3 copies of 3-OST-1 (E and F), and 6-OST-1 correctant of the mutant (G and H) were double-labeled with fluorescein-AT (A, C, E, and G) and Alexa 594-FGF-2 (B, D, F, and H) and subjected to dual-color FACS.

To determine whether the diminished 6-OST activity in the precursor mutant caused the precursor mutant's deficiency in AT binding, precursor mutant was transduced with 6-OST-1 cDNA. To create the 6-OST-1 cDNA, CHO 6-OST-1 coding region was amplified and sequenced from the CHO-K1 quick-clone cDNA library by PCR. Since only partial 6-OST-1 coding sequence from CHO cells has been reported (32), the complete CHO 6-OST-1 sequence was deposited in Genbank (accession number: AB006180). Stable 6-OST-1 transfectants were screened by FACS. Specifically, the cells were labeled with fluorescein-AT and Alexa 594-FGF-2 and then subjected to dual-color FACS. The FACS analysis for a correctant cell is shown in FIG. 5, at panels G and H. The correctants with high AT binding affinity were single-cell-cloned. HS[$^{35}$S] from correctants was isolated by AT-affinity chromatography and analyzed The correctant produced HS and HS$^{act}$. Surprisingly, approximately between 28% and 50% of total HS produced by the correctant was HS$^{act}$. The only cultured cell known to the applicants at the time of the filing the instant application produces approximately 0%-1%$^{HSact}$.

Example 6

Figure 6:
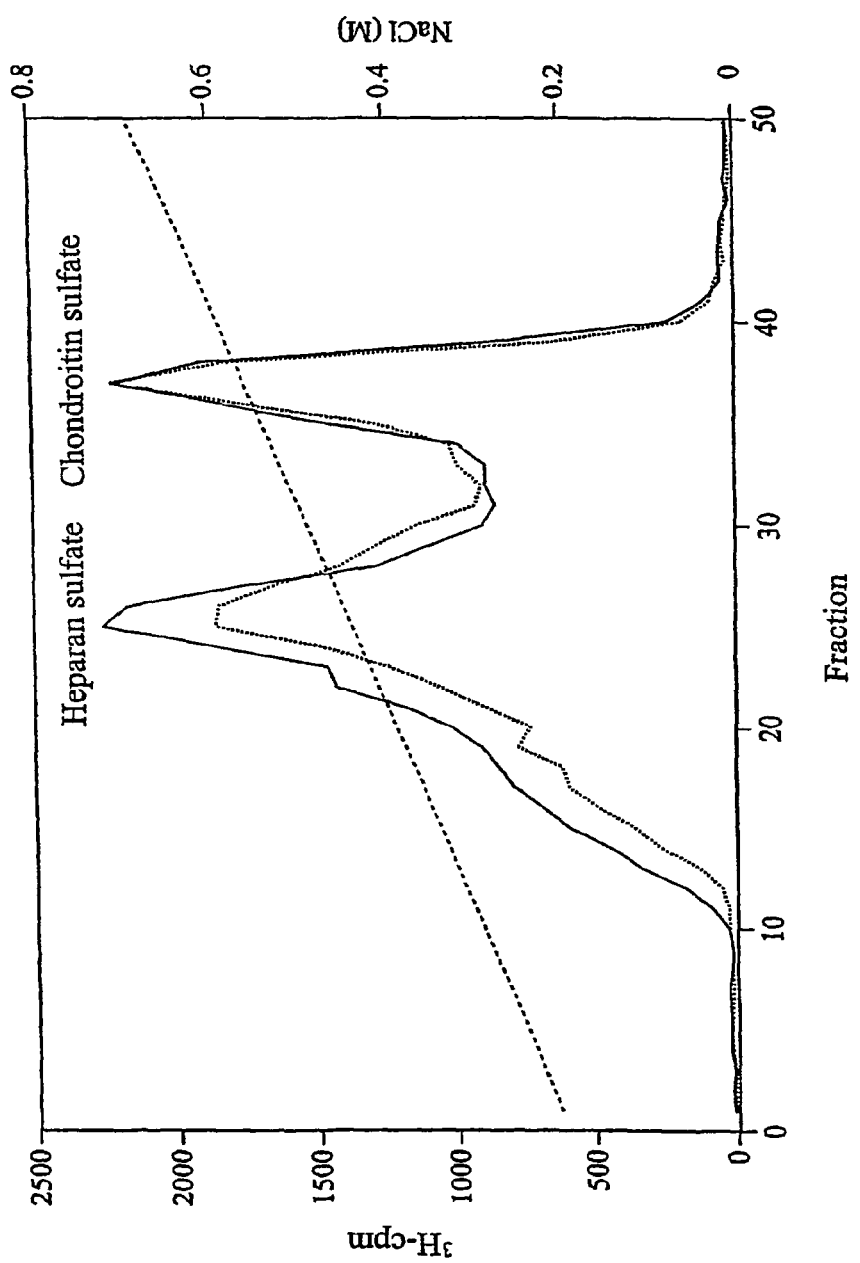
FIG. 6 depicts HPLC anion-exchange chromatography of GAGs. The HPLC anion-exchange was performed as follows. [$^3$H]GlcN-Labeled GAG chains from wild-type and mutant were isolated by protease digestion and β-elimination. Samples were analyzed by HPLC anion-exchange chromatography. Solid tracer, mutant; broken tracer, wild-type. The broken line indicates the concentration gradient of sodium chloride.
Figure 7:
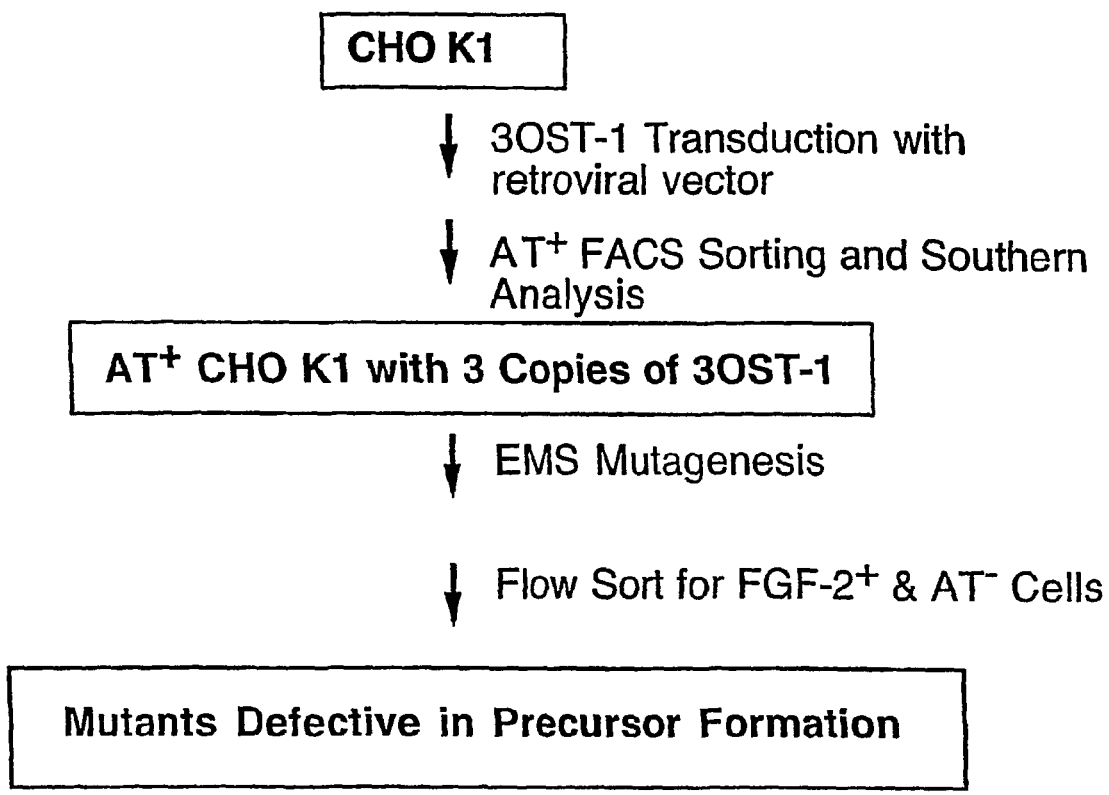
FIG. 7 illustrates one embodiment of a method for elucidating the HS$^{act}$ biosynthetic pathway. In this embodiment, using recombinant retroviral transduction, the human heparan sulfate (HS) 3-O-sulfotransferase 1 (3-OST-1) gene was transduced into Chinese hamster ovary (CHO) cells. 3-OST-1 expression gives rise to CHO cells with the ability to produce anticoagulant HS (HS$^{act}$). A cell line containing 3 copies of 3-OST-1 was chosen by Southern analysis. After chemical mutagenesis of this cell line, FGF-2 binding positive and AT binding negative mutant cells were FACS sorted and cloned. The advantage of having 3 copies of 3-OST-1 is that upstream genes that are responsible for generating specific HS precursor structures can be sought after chemical mutagenesis without being concerned with the loss of 3-OST-1. FGF-2 selection is employed to make certain that the mutant cells still make HS.

Correctant Cells Produce a Greater Percentage of GlcNac6S and GlcNS6S Residues In Vivo than Either the Wild-Type CHO Cells Expressing 3-OST-1 and the Precursor Mutant Cells The disaccharide composition of the HS derived from correctant cells was shown to a comprise a greater percentage of GlcNAc6S and GlcNS6S residues than CHO cells or mutant cells as follows. HS[$^{35}$S] from 3-OST-1 expressing CHO cells, precursor mutant cells and correctant cells was isolated and digested with a mixture of heparitinases. The resulting disaccharides were independently separated on a Bio-Gel P2 column and further resolved by IPRP-HPLC (FIG. 6). The relative percentages are set forth below.

TABLE 4

| Disaccharide | Wild-type | Precursor mutant | Correctant |
|---|---|---|---|
| GlcNAc6S | 7% | 5% | 9% |
| GlcNS6S | 9% | 4% | 13% |

Precursor Mutant

The present disclosure also provides a method, which constitutes a general approach for defining and obtaining components of biosynthetic pathways when (1) the gene for a downstream or terminal biosynthetic enzyme has been isolated, and (2) an assay for the downstream product(s) is available. This method of delineating biosynthetic pathways comprises placing multiple copies of the gene for a down-stream component of the pathway (i.e., a component acting at or near the end of a biosynthetic pathway) into a target cell line to produce a multi-expresser; mutagenizing the multi-expresser to obtain mutants deficient in up-stream component (i.e., components that generate precursor structures earlier in the pathway than the downstream component); and analyzing the precursor mutants. In some embodiments the method further comprises "correcting" the precursor mutant, for example, by transducing the mutant with the gene encoding a putative precursor protein. The transduction may be accomplished using one or more previously identified components of the biosynthetic pathway or using a "shotgun" library approach. In other embodiments, the correction may entail contacting the precursor mutant with the gene products of the biosynthetic pathway and screening for the phenotype of the wild-type, for example, ligand binding.

The advantage of a cell line containing multiple copies of a terminal or downstream gene product is that the activity of the downstream gene product remains intact following mutagenesis, therefore, upstream gene products will determine the phenotype of the mutagenized cell. Thus, the present invention provides methods of generating mutants specifically defective for upstream gene products, as well as, methods for isolating downstream components and delineating biosynthetic pathways.

Example 7

Creation of Precursor Mutant

To elucidate $HS^{act}$ biosynthesis, mutants defective in the formation of $HS^{act}$ precursors were created. Chinese hamster ovary (CHO) cells were selected as the target cell because wild-type CHO cells produce $HS^{inact}$ but not $HS^{act}$ (presumably, due to lack of HS 3-O-Sulfotransferase-1 (3-OST-1) expression). Furthermore, a series of HS biosynthetic mutants have been successfully made in CHO cells (23-28).

The 3-OST-1 gene, which was presumed to be the terminal enzyme in the $HS^{act}$ biosynthetic pathway, was introduced into CHO cells by retroviral transduction (29). 3-OST-1 expression gave rise to CHO cells with the ability to produce $HS^{act}$. A CHO cell line containing 3 copies of 3-OST-1 (referred to herein as "3-OST-1 expressing CHO cells, "3-OST-1 triple mutant" or "multi-expresser") was selected for further analysis and experimentation. The 3-OST-1 triple mutant was subjected to chemical mutagenesis. Cells positive for the desired knockout phenotype, specifically, positive for HS expression (selected by FGF-2 binding) and negative for $HS^{act}$ expression (selected by AT binding), were identified and isolated (FIG. 5, panels E and F). This cell line is referred to herein as the "6-OST-1 deficient mutant" or "precursor mutant."

The precursor mutant disclosed herein, which makes decreased amounts of 6-O-sulfated residues, is defective in AT binding (FIG. 5E) due to decreased 6-O-sulfotransferase activities. The defect in this mutant has been corrected, both in vivo (by transduction with a 6-OST-1 gene) and in vitro (by contacting HS with 6-OST-1 protein).

Example 8

Correction of the Precursor Mutant

The 6-OST-1 sulfate defect of the 6-OST-1 deficient mutant was corrected (i.e., the phenotype of the parental cell line was recovered) by transduction with 6-O-sulfotransferase-1 gene (FIG. 5, panels G and H). The resultant cell line (the "Correctant") produced HS, 50% of which is $HS^{act}$. Previously reported cell lines have been observed to produce less than 1% $^{HSact}$. This represents the highest percentage of $HS^{act}$ production by any reported cell line. Thus, the present invention provides for a cell line that produces high yields of $HS^{act}$, as well as methods of efficiently producing $HS^{act}$. This cell line (termed "hyper-producer") expresses approximately 28%-50% of $HS^{act}$ relative to $HS^{total}$.

Example 9

GAGs from Precursor Defective Mutant and Wild-Type CHO Cells have Similar Charge Densities GAGs from the 3-OST-1 expressing CHO cells and precursor mutant cells were isolated and analyzed by biosynthetic labeling studies using [6-$^3$H]GlcN. HPLC anion-exchange analysis of the [$^3$H]GAG chains from the precursor mutant resolved HS (0.31-0.50 M NaCl) from chondroitin sulfate (0.52-0.60 M NaCl) (FIG. 6). The GAG chains from the 3-OST-1 expressing CHO cells (FIG. 6, solid tracer) resolved into a similar profile to that of the precursor mutant (FIG. 6, broken tracer). This result implies that the HS from the precursor mutant and the 3-OST-1 expressing CHO cells have similar charge densities charge density and therefore, the decrease in AT-binding activity observed in the precursor mutant may be attributed to structural changes in the HS, possibly due to differences in degree of sulfation.

Example 10

Precursor Mutant Makes Less 6-O-Sulfate Containing Disaccharides than 3-OST-1 Expressing CHO Cells Since HS from the precursor mutant has similar charge density to that of the 3-OST-1 expressing CHO cells, the decrease in AT binding in the precursor mutant was expected to correlate with a change in the structure of the HS chains. The GAGs synthesized by the 3-OST-1 expressing CHO cells and precursor mutant were analyzed by biosynthetic labeling studies using [$^{35}$S]sulfate. The 3-OST-1 expressing CHO cells and precursor mutant cells produced the same amount of [$^{35}$S]HS and both samples contained ~70% HS and ~30% chondroitin sulfate (data not shown). This ratio of HS to chondroitin sulfate is consistent with the result shown in FIG. 6 (wherein HS accounted for 68% of the GAGs in the precursor mutant, and HS accounted for 66% of the GAGs in the 3-OST-1 expressing CHO cells). [$^{35}$S]sulfate labeled HS chains from the 3-OST-1 expressing CHO cells and precursor mutant cells were then digested with a mixture of heparitinases. The resulting disaccharides (representing approximately 93% of total [$^{35}$S]sulfate counts) were separated on a Bio-Gel P2 column and further resolved by IPRP-HPLC with appropriate internal standards. As Table 5 shows, the precursor mutant cells produced reduced amounts of 6-O-sulfated disaccharides relative to the 3-OST-1 expressing CHO cells.

TABLE 5

Disaccharide Composition

| Disaccharide | 3-OST-1 expressing CHO cells | Precursor Mutant | Correctant |
|---|---|---|---|
| ΔUA-GlcNS | 30% | 35% | 27% |
| ΔUA-GlcNAc6S | 7% | 5% | 9% |
| ΔUA-GlcNS6S | 9% | 4% | 13% |
| ΔUA2S-GlcNS | 20% | 36% | 22% |
| ΔUA2S-GlcNS6S | 34% | 19% | 29% |

Example 11

Precursor Mutant and 3-OST-Expressing CHO Cells Express 6-OST-1 mRNA, but not 6-OST-2 mRNA or 6-OST-3 mRNA In order to explain the reduced levels of 6-O-sulfate containing disaccharides in the precursor mutant, 6-OST-1 isoform expression in 3-OST-1 expressing CHO cells was compared with 6-OST-1 isoform expression in the precursor mutant cells. Human 6-OST-1, 6-OST-2, and 6-OST-3 cDNA were used as probes in Northern blot and RT-PCR studies. Northern analysis indicated that the precursor mutant and the 3-OST-1 expressing CHO cells have the same level of 6-OST-1 mRNA. However, no 6-OST-2 or 6-OST-3 mRNA was detected in either the 3-OST-1 expressing CHO cells or the precursor mutant cells, indicating that CHO cells express 6-OST-1 only.

The expression pattern for 6-OST isoforms in CHO cells was confirmed using RT-PCR analysis of 3-OST-1 expressing CHO cells and precursor mutant cells. One set of PCR primers for 6-OST-1, three sets of PCR primers for 6-OST-2, and two sets of PCR primers for 6-OST-3 were used to evaluate mRNA expression of the 6-OST isoforms. The same level of 6-OST RT-PCR products was observed for both 3-OST-1 expressing CHO cells and the precursor mutant cells; however, no RT-PCR products were observed in either cell from the three sets of 6-OST-2 RT-PCR reactions and two sets of 6-OST-3 RT-PCR reactions. The Northern blot and RT-PCR analyses described above demonstrate that CHO cells express 6-OST-1, but not 6-OST-2 or 6-OST-3.

Example 12

The Coding Region of 6-OST-1 in the Precursor Mutant Contains No Point Mutations Northern blot and RT-PCR analysis indicated that the precursor mutant cells and the 3-OST-1 expressing CHO cells express similar levels of 6-OST-1 mRNA, however, as described in greater detail below, the level of 6-OST-1 activity in the precursor mutant is lower than the level of activity in the 3-OST-1 expressing CHO cells. This observation raised the possibility that the precursor mutant CHO cells might have one or more point mutation(s) in 6-OST-1 gene that diminishes the level of 6-OST sulfotransferase activity. The coding regions of 6-OST-1 RT-PCR products from the mutant were double-strand-sequenced and no point mutation was observed compared to wild-type 6-OST-1. Thus, the diminished level of 6-OST activity observed is not due to a defect in the 6-OST-1 gene in the precursor mutant.

Example 13

Precursor Mutant has Decreased 6-O-Sulfotransferase Activities Compared to Wild-Type CHO Cells FACS analysis showed that the precursor mutant cells were defective in AT binding (FIG. 5, panel E). The coding sequence of 6-OST-1 was not mutated and 6-OST-1 mRNA expression levels were normal; however, disaccharide compositional studies demonstrated that the precursor mutant made less 6-O-sulfated residues in vivo than wild-type CHO cells.

The 6-O-sulfotransferase activity of the precursor mutant was evaluated in vitro. Crude cell homogenates from wild-type CHO cells and precursor mutant CHO cells served as the source of 6-OST-1 enzyme. HS derived from wild-type CHO cells, N,O-desulfated, re-N-sulfated heparin (CDSNS-heparin), and 6-O-desulfated heparin was incubated with 6-OST-1 enzyme from wild-type CHO cells and precursor mutant in the presence of a sulfate donor. The resulting reaction products were digested by a combination of heparitinases, followed by Bio Gel P2 chromatography. The disaccharides collected were then subjected to IPRP-HPLC analysis. Both 2-O-[$^{35}$S]sulfate (control) and 6-O-[$^{35}$S]sulfate labeled disaccharides resulting from the 6-OST-1 enzymes were quantitated. 2-O-sulfotransferase activity was similar in precursor mutant cells (118±3 pmol/min/mg) and the wild-type CHO cells (122±2 pmol/min/mg) when CDSNS-heparin was used as substrate (not shown). However, a 30% to 39% reduction of 6-O-sulfotransferase activity was observed in the precursor mutant relative to the wild-type CHO cells with all three substrates (Table 6).

TABLE 6

6-O-sulfotransferase activity (pmol/min/mg)

| Substrate | Wild-type CHO | Precursor Mutant | % reduction of wild-type activity in precursor mutant |
|---|---|---|---|
| HS (CHO K1) | 5.6 ± 0.3 | 3.9 ± 0.4 | 30% |
| 6-O-desulfated heparin | 4.4 ± 0.3 | 2.7 ± 0.5 | 39% |
| CDSNS-heparin | 11 ± 2 | 7 ± 1 | 38% |

Example 14

Size Exclusion Chromatography Coupled with Mass Spectrometry is Effective for Compositional Analysis of Oligosaccharides Mass spectrometric detectors produce far more information than conventional UV or fluorescent detectors and allows the monosaccharide composition of individual components to be determined (39). Introducing stable isotope PAP$^{34}$S into the 3-O-position of HS by pure 3-OST-1, a 3-O-sulfate containing disaccharide with a unique mass was identified using a combination of capillary IPRP-HPLC coupled with mass spectrometry. The method consumes 0.5 μg of total HS for separating and detecting different HS disaccharides. This method provides a practical way of accomplishing HS disaccharide analysis of general HS samples from cells or tissues without radioisotope labeling. Furthermore, biologically inactive HS oligosaccharides could be treated in vitro with different pure sulfotransferases plus stable sulfur isotope PAPS (e.g., PAP$^{33}$S and PAP$^{34}$S). The different stable isotope tagged biologically active oligosaccharides could then be sequenced by a combination of capillary IPRP-HPLC for separation and mass spectrometry. In this manner, biologically critical regions can be pinpointed and sequenced.

Capillary IPRP-HPLC coupled with mass spectrometry. Heparin molecules exhibiting a high affinity for a synthetic peptide (CRPKAKAKAKAKDQTK) (SEQ ID NO. 7) mimicking a heparin-binding domain of heparin interacting protein (HIP) also show an extremely high affinity for AT (37). It was expected that inclusion of this small peptide in the heparitinase digestion solution would protect 3-O-[$^{35}$S]sulfate labeled HS from degrading into tetrasaccharide. Theoretically, HIP peptide-protected, AT binding HS oligosaccharides would be recovered. However, in the presence of the HIP peptide, all the 3-O-[$^{35}$S]sulfate labeled sugars were degraded into disaccharides instead of oligosaccharides or tetrasaccharides as judged by their elution position on Bio-Gel P2 and their unique elution positions on IPRP-HPLC (the major 3-O-[$^{35}$S]sulfate containing disaccharides eluted right before ΔUA-GlcNS6S disaccharide standard). Because there is no ΔUA-GlcNS3S standard reported, the structure was verified. Stable, isotope PAP$^{34}$S was made. The PAP$^{34}$S (99% isotope purity determined by ES-MS) was prepared by incubating ATP and stable isotope Na$_2$$^{34}$SO$_4$ (Isonics Corp.) with ATP sulfurylase (Sigma), adenosine 5'-phosphosulfate kinase (a generous gift from Dr. Irwin H. Segel), and inorganic pyrophosphatase (Sigma) (38). HS chains from wild-type CHO cells were labeled with pure 3-OST-1 plus PAP$^{34}$S. A capillary IPRP-HPLC (LC Packings) method for separating HS disaccharides was developed. This method is similar to conventional IPRP-HPLC (29) except using 5 mM dibutylamine as an ion pairing reagent (Sigma), and then coupled it to an ESI-TOF-MS (Mariner Workstation, PerSeptive Biosystems, Inc.) to detect the mass of each disaccharide eluted. Six HS disaccharide standards from Seikagaku were separated by capillary HPLC and detected by negative polarity ESI-MS. The accuracy of the ES-MS is ±0.001 m/z unit after calibration with the molecular standard sets supplied by the manufacture (Bis TBA, Heptadecafluronononanoic acid, Perflurotetradecanoic acid). 3-O-$^{34}$S-labeled HS was digested with a combination of 1 mU of each heparitinase I, heparitinase II, heparitinase IV, and heparinase in the absence or presence of 0.5 mg/ml HIP peptide. 0.5 μg of digested HS was injected into capillary HPLC coupled with mass spectrometry (FIG. 8). UV peak B eluted at the same time as a ΔUA-GlcNS6S standard, whereas UV peak D eluted at the same time as a ΔUA2S-GlcNS standard (FIG. 8, panel A). Three major ions with m/z 247.5, 496.0, and 625.2 were observed in both UV peaks (FIG. 3, panel B and D), where 496.0 is z1 (−1) charged, 247.5 is z2 (−2) charged, and 625.2 is one dibutylamine adducted, z1 (−1) charged ΔUA-GlcNS6S or ΔUA2S-GlcNS disaccharides. However, when m/z regions 494.0 to 501.0 from both peal B and peak D were expended (panel C and panel E), a non-natural abundant, z1 charged molecular ion with m/z 498.0 was observed in UV peal B, but not in UV peak D. 498.0 vs. 496.0 of disaccharide ions should represent ΔUA-GlcNS3[$^{34}$5]S and ΔUA-GlcNS6S, respectively. The mass for ΔUA-GlcNS3[$^{34}$]S is barely detectable in the absence of HIP peptide, which is consistent with the literature that 3-O-sulfate containing sugars are usually degraded into tetrasaccharides not disaccharides by a mixture of heparitinase digestion (20,33). HIP peptide was included in heparitinase digestion when 3-O-containing HS were degraded into disaccharides.

Materials and Methods for Practicing the Inventions Exemplified Above

Cell Culture. Wild-type Chinese hamster ovary cells (CHO-K1) were obtained from the American Type Culture Collection (CCL-61; ATCC, Rockville, Md.). CHO cells were maintained in Ham's F-12 medium supplemented with 10% fetal bovine serum (HyClone), penicillin G (100 units/ml), and streptomycin sulfate (100 μg/ml) at 37 C under an atmosphere of 5% CO$_2$ in air and 100% relative humidity. The cells were passaged every 34 days with 0.125% (w/v) trypsin and 1 mM EDTA, and after 10-15 cycles, fresh cells were revived from stocks stored under liquid nitrogen. Low-sulfate medium was composed of Ham's F-12 medium supplemented with penicillin G (100 units/ml) and 10% fetal bovine serum that had been dialyzed 200-fold against phosphate-buffered saline (30). Low-glucose Ham's F-12 medium contained 1 mM glucose supplemented with penicillin G (100 units/ml), streptomycin sulfate (100 μg/ml), and fetal bovine serum that had been dialyzed 200-fold against phosphate-buffered saline (30). All tissue culture media and reagents were purchased from Life Technologies (Gaithersburg, Md.) unless otherwise indicated.

3-OST-1 recombinant retroviral transduction. The retrovirus plasmid pMSCVpac was obtained from Dr. Robert Hawley, University of Toronto (31). pCMV3-OST-1 was digested with BglII and XhoI to release the wild-type murine 3-OST-1 cDNA (15). The cDNA fragment (1,623 bp) was cloned into the BglII+XhoI sites in pMSCVpac. All plasmid DNA prepared for transfection was made with the Invitrogen SNAP-MIDI kit according to the manufacturer's directions. Infectious virions were produced by transducing ecotropic PHOENIX packaging cells with recombinant provirus plasmids using the calcium phosphate transfection technique. Following the precipitation step, the cells were re-fed with 2 ml/well of flesh DMEM and incubated overnight. Viral supernatants were collected, either flash-frozen in liquid nitrogen, and stored at −80° C. or used directly after low-speed centrifugation.

Wild-type CHO cells containing ecotropic receptors were treated with trypsin and then plated at 150,000 cells/well in a 6-well dish. One day later, target cells (<70% confluent) were incubated overnight with viral supernatants containing 5 μg/ml Polybrene surfactant. After 12 hours, the virus containing media was replaced with fresh growth media. Wild-type CHO cells were exposed to recombinant retrovirus three times and selected and maintained in 7.5 μg/ml puromycin (Sigma).

Antithrombin and FGF-2 labeling. The standard reaction mixture for preparing fluorescent AT contained 20 mM NaH$_2$PO$_4$ (pH 7.0), 0.3 mM CaCl$_2$, 25 μg of PBS dialyzed AT (GlycoMed), 4 mU neuraminidase (Worthington Biochemical Corp.), 4 mU galactose oxidase (Worthington Biochemical Corp.), and 125 μg/ml fluorescein hydrazide (Molecular Probe, C-356) in a final volume of 280 μl. The mixtures were incubated at 37° C. for 1 h. PBS (1 ml) and a 50% slurry of heparin-Sepharose in PBS (100 μl) was added and mixed end-over-end for 20 min. After centrifugation, the heparin-Sepharose beads were washed 4 times with PBS (1 ml). Labeled AT was eluted with four 0.25 ml aliquots of 10× concentrated PBS and desalted by centrifugation for 35 minutes at 14,000 rpm through two Microcon-10 columns (Millipore). The concentrated AT was diluted with 0.5 ml 10% FBS in PBS containing 2 mM EDTA and used directly for cell labeling studies.

Fluorescent FGF-2 was prepared by mixing 50 μl of 1 M sodium bicarbonate to 0.5 ml of PBS containing 2 mg/ml BSA and 3 μg FGF-2. The mixture was then transferred to a vial of reactive dye (Alexa 594, Molecular Probes) and stirred at room temperature for 1 hour. The isolation of the labeled FGF-2 was identical to that described above for labeled AT.

Cell sorting. Nearly confluent monolayers of 3-OST-1 transduced CHO K1 cells were detached by adding 10 ml of 2 mM EDTA in PBS containing 10% FBS and centrifuged. The cell pellets were placed on ice and 50 µl each of fluorescein-AT and Alexa 594-FGF-2 were added. After 30 minutes, the cells were washed once and resuspended in 1 ml of 10% FBS in PBS containing 2 mM EDTA. Flow cytometry and cell sorting was performed on FACScan and FACStar instruments (Becton Dickinson) using dual color detection filters. AT and FGF-2 binding positive cells were sorted and subsequently single-cell cloned into a 96 well plate. The single cell clones were expanded and frozen for further analysis.

Twelve 3-OST-1 transduced CHO K1 clones were obtained as described above. The number of copies of 3-OST-1 in the individual clones was determined by Southern analysis as follows. Genomic DNA (10 µg) was digested with 40 U of EcoRI overnight at 37° C., electrophoresed on a 0.7% (w/v) agarose gel, transferred to GeneScreen Plus (NEN) and probed with 3-OST-1 cDNA labeled with the Megaprime labeling kit (Amersham). Blots were hybridized in ExpressHyb Solution (Clontech) containing 3-OST-1 probe ($2\times10^6$ cpm/ml), followed by autoradiography. The cell clone with 3 copies of 3-OST-1 was expanded and frozen for further studies.

Mutant screening. Wild-type CHO with 3 copies of 3-OST-1 were mutagenized with ethylmethane sulfonate as described in the literature (31) and frozen under liquid nitrogen. A portion of cells was thawed, propagated for 3 days, and labeled with both Alexa 594-FGF-2 and fluorescein-AT. The labeled cells were sorted and FGF-2 positive and AT negative cells were collected. Approximately $1\times10^4$ sorted cells were collected into 1 ml of complete F-12 Ham's media, then plated in T-75 flasks. Sorted cell populations were maintained in complete F-12 Ham's medium for one week, then the cells were labeled and sorted again as described above. After 5 rounds of sorting, FGF-2 positive and AT negative cells were single-cell-sorted into a 96 well plate. The single cell clones were expanded and frozen for further analysis. The sorting profiles of CHO K1 with 3 copies of 3-OST-1, precursor mutant, and the 6-OST-1 correctant of the mutant were shown by dual-color fluorescence flow cytometric analysis in FIG. 5.

HS Preparation and analysis. Cell monolayers were labeled overnight with 100 µCi/ml of carrier free sodium [$^{35}$S]sulfate (ICN) in sulfate deficient DMEM, supplemented with penicillin G (100 Units/ml), and 10% (v/v) dialyzed FBS. The proteoglycan fraction was isolated by DEAE-Sepharose chromatography and beta-eliminated in 0.5 M NaBH$_4$ in 0.4 M NaOH at 4° C. overnight. The samples were neutralized with 5 M acetic acid until bubble formation ceased and the released chains were purified by another round of DEAE-Sepharose chromatography followed by ethanol precipitation. The pellet from centrifugation was washed with 75% ethanol and resuspended in water. The GAGs were digested with 20 mU of chondroitinase ABC (Seikagaku, Inc.) in buffer containing 50 mM Tris-HCl and 50 mM sodium acetate (pH 8.0). Complete digestion of chondroitin sulfate by chondroitinase ABC was assured by monitoring the extent of conversion of the carrier to disaccharides (100 µg=1.14 absorbance units at 232 nm). HS was purified from chondroitinase degraded products by phenol/chloroform (1:1, v/v) extraction and ethanol precipitation. After washing the pellets with 0.5 ml of 75% ethanol, the HS was dissolved in water for further analysis.

cDNA cloning and expression of CHO 6-OST-1. Sequences coding for CHO 6-OST-1 were amplified from a CHO K1/cDNA quick-clone library (Clontech). The reaction mixture contained 2 units pfu polymerase (Stratagene), 1 ng of cDNA, and 100 pmol of the Primers. The sense primer has an added Bgl II site (5'GCAGATCTGCAGGACCATGGT-TGAGCG CGCCA GCAAGTTC-3') (SEQ ID NO. 8) and the antisense primer has an added Xba I site (5'-GCTCTAGAC-TACCACT TCTCAATGATGTGGCTC-3') (SEQ ID NO. 9). The 6-OST-1 primer sequences are derived from the human 6-OST-1 cDNA sequence (from residue 240 to 264) and to the complement of this sequence (from residue 1147 to 1172) as reported (32). After 30 thermal cycles (1 min of denaturation at 94° C., 2 min of annealing at 55° C., 3 min of extension at 72° C.), the amplification products were analyzed in 1% agarose gels and detected by ethidium bromide staining. The amplification products were excised from the gel and cleaned by Gel Extraction kit (Qiagen). The PCR product was treated with Bgl II and Xba I, ligated into Xba I and BamHI digested pInd/Hygro plasmid (Clontech) and transformed into E. coli DH5α competent cells. Four clones from each of two separate PCR reactions were sequenced and found to be identical. pind/Hygro 6-OST-1 containing plasmid was transfected into the CHO mutant cells. AT and FGF-2 binding positive cells were sorted and subsequently single-cell-cloned into a 96 well plate. The single cell clones were expanded and frozen for further analysis.

6-O-sulfation of HS in vitro. The standard reaction mixture contained 50 mM MES (pH 7.0), 1% (w/v) Triton X-100, 5 mM MnCl$_2$, 5 mM MgCl$_2$, 2.5 mM CaCl$_2$, 0.075 mg/ml protamine chloride, 1.5 mg/ml BSA, either metabolically labeled [$^{35}$S]HS or non-radioactive HS chains, cold PAPS (0.5 mM) or [$^{35}$S]PAPS (25 µM, $2\times10^7$ cpm), and 70 ng of purified baculovirus-expressed human 6-OST-1 in a final volume of 50 µl. The mixtures were incubated either 20 minutes or overnight at 37° C., and 200 µg of chondroitin sulfate C was added. HS chains were purified by phenol/chloroform extraction and anion exchange chromatography on 0.25-ml columns of DEAE-Sephacel packed in 1 ml syringes (20). After ethanol precipitation, the pellets were washed with 75% ethanol, dried briefly under vacuum, and dissolved in water for further analysis.

Separation of HS$^{act}$ and HS$^{inact}$ by AT-affinity chromatography. AT-HS complexes were created by mixing 3-O-sulfated HS in 500 µl of HB buffer (150 mM NaCl, 10 mM Tris-Cl (pH 7.4)) with 2.5 mM AT, 100 µg of chondroitin sulfate, 0.002% Triton-X 100, and 1 mM each of CaCl$_2$, MgCl$_2$, and MnCl$_2$ (18). HB containing ~50% slurry of Concanavalin A-Sepharose 4B (60 µl) was then added. AT complexes were bound to Concanavalin A by way of the Asn-linked oligosaccharides. After one hour end-over-end rotation at 4° C., the beads were sedimented by centrifugation at 10,000×g. The supernatant was collected and the beads were washed three times with 1.25 ml of HB containing 0.0004% Triton-X 100. The supernatant and washing solutions contained HS$^{inact}$. The HS$^{act}$ was eluted with three successive washes with 100 µl HB containing 1 M NaCl and 0.0004% Triton-X 100. After adding 100 µg of chondroitin sulfate as carrier to HS$^{act}$, the sample was extracted with an equal volume of phenol/chloroform, followed by chromatography on DEAE-Sepharose and ethanol precipitation. The pellets were washed with 75% ethanol, dried briefly under vacuum and dissolved in water.

Disaccharide analysis of HS. Heparitinase I (EC. 4.2.2.8), heparitinase II (no EC number), and heparinase (EC. 4.2.2.7) were obtained from Seikagaku heparitinase IV was obtained from Dr. Yoshida, Seikagaku Corporation, Tokyo. Heparitinase I recognizes the sequences: GlcNAc/NS±6S(3S?)-↓GlcUA-GlcNAc/NS±6S. The arrow indicates the cleavage site. Heparitinase II has broad sequence recognition: GlcNAc/NS±6S(3S?)-↓GlcUA/IdoUA±2S-GlcNAc/NS±6S. Heparinase(heparitinase III) and heparitinase IV recognize the sequences: GlcNS±3S±6S-↓IdoUA2S/GlcUA2S-GlcNS±6S. The reaction products and references can be found in the following references (33,34). The digestion of $HS^{act}$ was carried out in 100 μl of 40 mM ammonium acetate (pH 7.0) containing 3.3 mM $CaCl_2$ with 1 mU of heparitinase I or 1 mU of each heparitinase I, heparitinase II, heparitinase IV, and heparinase (heparitinase III). The digestion was incubated at 37° C. overnight unless otherwise indicated. For low pH nitrous acid degradation, radiolabeled HS samples were mixed with 10 μg bovine kidney HS (ICN) and digested (35).

Disaccharides were purified by Bio-Gel P2 chromatography and resolved by ion pairing reverse-phase HPLC with appropriate disaccharide standards (36). Bio-Gel P2 or P6 columns (0.75×200 cm) were equilibrated with 100 mM ammonium bicarbonate. Radiolabeled samples (200 μl) were mixed with Dexdran blue (5 μg) and phenol red (5 μg) and loaded on the column. The samples were eluted at a flow rate of 4 ml/hour with collection of 0.5 ml fractions. The desired fractions were dried under vacuum, individually or pooled to remove ammonium bicarbonate.

Capillary IPRP-HPLC coupled with mass spectrometry. Heparin molectiles exhibiting a high affinity for a synthetic peptide (CRPKAKAKAKAKDQTK) I SEQ ID NO. 7) mimicking a heparin-binding domain of heparin interacting protein (HIP) also show an extremely high affinity for AT (37). It was expected that inclusion of this small peptide in the heparitinase digestion solution would protect 3-O-[$^{35}$S]sulfate labeled HS from degrading into tetrasaccharide. Theoretically, HIP peptide-protected, AT binding HS oligosaccharides would be recovered. However, in the presence of the HIP peptide, all the 3-O-[$^{35}$S]sulfate labeled sugars were degraded into disaccharides instead of oligosaccharides or tetrasaccharides as judged by their elution position on Bio-Gel P2 and their unique elution positions on IPRP-HPLC (the major 3-O-[$^{35}$S]sulfate containing disaccharides eluted right before ΔUA-GlcNS6S disaccharide standard). Because there is no ΔUA-GlcNS3S standard reported, the structure was verified. Stable isotope $PAP^{34}S$ was made. The $PAP^{34}S$ (99% isotope purity determined by ES-MS) was prepared by incubating ATP and stable isotope $Na_2^{34}SO_4$ (Isonics Corp.) with ATP sulfurylase (Sigma), adenosine 5'-phosphosulfate kinase (a generous gift from Dr. Irwin H. Segel), and inorganic pyrophosphatase (Sigma) (38). HS chains from wild-type CHO cells were labeled with pure 3-OST-1 plus $PAP^{34}S$. A capillary IPRP-HPLC (LC Packings) method for separating HS disaccharides was developed. This method is similar to conventional IPRP-HPLC (29) except using 5 mM dibutylamine as an ion pairing reagent (Sigma), and then coupled it to an ESI-TOF-MS (Mariner Workstation, PerSeptive Biosystems, Inc.) to detect the mass of each disaccharide eluted. Six HS disaccharide standards from Seikagaku were separated by capillary HPLC and detected by negative polarity ESI-MS. The accuracy of the ES-MS is ±0.001 m/z unit after calibration with the molecular standard sets supplied by the manufacture (Bis TBA, Heptadecafluorononanoic acid, Perflurotetradecanoic acid). 3-O-$^{34}$S-labeled HS was digested with a combination of 1 mU of each heparitinase I, heparitinase II, heparitinase IV, and heparinase in the absence or presence of 0.5 mg/ml HIP peptide. 0.5 μg of digested HS was injected into capillary HPLC coupled with mass spectrometry (FIG. 8). UV peal B eluted at the same time as a ΔUA-GlcNS6S standard, whereas UV peak D eluted at the same time as a ΔUA2S-GlcNS standard (FIG. 8, panel A). Three major ions with m/z 247.5, 496.0, and 625.2 were observed in both UV peaks (FIG. 3, panel B and D), where 496.0 is z1 (−1) charged, 247.5 is z2 (−2) charged, and 625.2 is one dibutylamine adducted, z1 (−1) charged ΔUA-GlcNS6S or ΔUA2S-GlcNS disaccharides. However, when m/z regions 494.0 to 501.0 from both peak B and peak D were expended (panel C and panel E), a non-natural abundant, z1 charged molecular ion with m/z 498.0 was observed in UV peak B, but not in UV peak D. 498.0 vs. 496.0 of disaccharide ions should represent ΔUA-GlcNS3[$^{34}$5]S and ΔUA-GlcNS6S, respectively. The mass for ΔUA-GlcNS3[$^{34}$S]S is barely detectable in the absence of HIP peptide, which is consistent with the literature that 3-O-sulfate containing sugars are usually degraded into tetrasaccharides not disaccharides by a mixture of heparitinase digestion (20,33). HIP peptide was included in heparitinase digestion when 3-O-containing HS were degraded into disaccharides.

Northern blot hybridization and RT-PCR. To generate specific Northern blot hybridization probes, PCR primers were designed that bracket unique sequences within human 6-OST-1, 6-OST-2 and 6-OST-3. A 249 bp PCR product that corresponds to a region within the 3'-UTR of the 60ST-1 gene starting at position 1772 and ending at 2021 was used as an isoform specific probe. Similarly, a 299 bp PCR product that corresponds to a region in the 3'-UTR of the 60ST-2 gene starting at position 1831 and ending at 2130, and another product within the 3'-UTR of the 6-OST-3 gene starting at 943 and ending at 1378 (444 bp) were used as a probe. PCR was performed with α[32P] dCTP (NEN Life Science Products) and isoform-specific radio-labeled probes were purified on G-25 Sephadex spin columns (Boehringer Mannheim). Hybridizations were carried out as to the manufacturer's instructions using 2×10$^6$ cpm probe per ml of ExpressHyb solution (CLONTECH). After the hybridizations were complete, the blots were washed twice in 2×SSC containing 0.1% SDS and once with 0.1×SSC containing 0.1% SDS, all at room temperature. Blots were then washed with 0.1×SSC containing 0.1% SDS at 50° C. For blots hybridized with the 6-OST probe, this last wash was repeated twice at 65° C. The membranes were then subjected to autoradiography with BioMax imaging film (Kodak) with a BioMax MS intensifying screen (Kodak).

For RT-PCR, poly A purified or DNase I treated total RNA was used. Primer pairs were designed that bracket isoform specific regions within the human sequences for both 60ST-2, and 60ST-3. For 60ST-1, a 569 bp fragment corresponding to nt 54 (GCG TGC TTC ATG CTC ATC CT) (SEQ ID NO. 10) to 622 (GTG CGC CCA TCA CAC ATG T) (SEQ ID NO. 11) within the hamster sequence was used. For 60ST-2, PCR targets included regions starting at nt 23 (CTG CTG CTG OCT TTG GTG AT) (SEQ ID NO. 12) and 346 (GCA GAA GAA ATG CAC TTG CCA) (SEQ ID NO. 13) and ending at nt 1471 (GCC OCT ATC ACC TTG TCC CT) (SEQ ID NO. 14), 1491 (TCA TTG GTG CCA TTG CTG G) (SEQ ID NO. 15) and 1532 (TGA GTG CCA GTT AGC GCC A) (SEQ ID NO. 16). For 60ST-3, the targets included regions that start at nt 5 (CCG GTG CTC ACT TTC CTC TTC) (SEQ ID NO. 17) and 353 (TTC ACC CTC AAG GAC CTG ACC) (SEQ ID NO. 18) and end at nt 988 (GCT CTG CAG CAG GAT GGT GT) (SEQ ID NO. 19) and 1217 (GCT GGA AGA GAT CCT TCG CAT AC) (SEQ ID NO. 20). Total RNA was purified from wild-type and precursor mutant CHO-K1 cells using the RNeasy total RNA kit from Qiagen as to the manufacturer's instructions. RNA was quantitated by absorbance at 260 nm and 100 μg of total RNA was reacted with DNase I (Ambion) at 37° C. for 45 minutes, twice extracted with equal volumes of acid phenol/chloroform, precipitated in ethanol, and reconstituted in DEPC treated water. Further selection of poly-A plus RNA was carried out with the Oligotex mRNA kit (Qiagen). RNA integrity was checked after electrophoresis on a 1% agarose gel and all RT reactions were run with M-MLV reverse transcriptase (Ambion) according to manufacturer's instructions. PCR was performed with Super Taq polymerase (Ambion).

Baculovirus expression and Purification of 6-OST-1. Human 6-OST-1 recombinant baculovirus was prepared using the pFastBas HT donor plasmid modified by the insertion of honeybee mellitin signal peptide (36) and the Bac-to-Bac Baculovirus expression system (Life Technologies, Inc.) according to the manufacturer's protocol, except that recombinant bacmid DNA was purified using an endotoxin-free plasmid purification kit (Qiagen, Inc.) and transfection of Sf9 cells was scaled up to employ 3 µg of bacmid DNA and $6 \times 10^6$ exponentially-growing cells in a 100-mm dish. At day three post-transfection, baculovirus was precipitated from the medium with 10% PEG, 0.5 M NaCl at 12,000×g, re-suspended in 14 ml of medium, and applied to a 100-mm dish seeded with $1.5 \times 10^7$ Sf9 cells. Medium from the infected cells was harvested after 90 hours of growth at 27° C., centrifuged at 400×g, made to 10 M in Tris, adjusted to pH 8.0, and centrifuged at 4000×g. Clarified medium was diluted with an equal volume of cold 10 mM Tris-HCl, pH 8.0, and stirred for 30 minutes with 0.6 ml (packed volume) of Toyopearl 650M chromatographic media (TosoHaas). The heparin-sepharose was packed into a column (0.4×4.75 cm), washed with 5 ml of TCG 50 (10 mM Tris-HCl, pH 8.0, 2% glycerol, 0.6% CHAPS, 50 mM NaCl), eluted with 1.2 ml of TCG 1000 (as above, but 1 M in NaCl) containing 10 mM imidazole, and concentrated to 0.25 ml in a Microcon YM-10 centrifugal filter (Millipore Corp.).

Histidine-tagged recombinant 6-OST-1 was affinity purified by mixing the product eluted from heparin-sepharose for 90 minutes at 4° C. with NiNTA magnetic agarose beads (Qiagen, Inc.) and magnetically sedimented from 60 µl of suspension. The beads were washed twice with 0.125 ml of TCG 400 containing 20 mM imidazole and eluted twice with 0.03 ml of TCG 400 containing 250 mM imidazole. The combined elution fractions contained approximately 25% of the sulfotransferase activity present in the starting medium.

Bacterial expression and Unification of 6-OST-1. Expression vector pET15b was purchased from Novagen (Madison, Wis.). *E. coli* strains BL21 and DH5α were obtained through ATCC (Manassas, Va.). An Ase I restriction site was introduced at 211-216 bp and a BamHI restriction site was introduced at 1344-1349 bp of human 6-OST-1-1(32) by PCR. The 6-OST-1 gene was then ligated into Nde I and BamHI digested pET15b and transformed into competent *E. coli* strain DH5α. A BL21 colony containing 6-OST-1 in pET15b with confirmed sequence was used to inoculate 2 L of LB containing 100 µg/mL ampicillin. The cultures were shaken in flasks at 250 rpm at 37° C. When the optical density at 600 nm reached 1.2, 1 mM IPTG was added to the cultures. The cultures were then agitated at 250 rpm overnight at room temperature. The cells were pelleted at 5,000 rpm for 15 minutes. The supernatant was discarded and the cell pellet was resuspended in 40 mL of 20 mM Tris, 500 mM NaCl, 0.6% CHAPS, 1% glycerol, and 5 mM imidazole, pH 7.9 ("binding buffer"). The cells were homogenized, and the homogenate was centrifuged at 13,000 rpm for twenty minutes. The supernatant was filtered through 0.2 µm filter paper and loaded onto a BioCAD HPLC system (PerSeptive Biosystems, Cambridge, Mass.) and purified using $Ni^{2+}$ chelate chromatography. Briefly, the supernatant was loaded onto the column and washed with binding buffer until unbound material was washed off the column. Then, low affinity material was washed off the column using 20 mM Tris, 500 mM NaCl, 0.6% CHAPS, 1% glycerol, and 55 mM imidazole, pH 7.9 and 6-OST-1 was eluted from the column with 20 mM Tris, 500 mM NaCl, 0.6% CHAPS, 1% glycerol, and 500 mM imidazole, pH 7.9. The purity of the recombinant 6-OST-1 was determined using a silver stained protein gel.

The invention disclosed herein may be embodied in other specific forms without departing from the spirit or essential characteristics thereof. The foregoing embodiments are therefore to be considered in all respects illustrative rather than limiting of the disclosed invention. The scope of the invention is thus indicated by the appended claims rather than by the foregoing description, and all changes which within the meaning and range of equivalency of the claims are therefore intended to be embraced herein.

The following references are incorporated by reference ill their entirety.

1. Aikawa, J., Grobe, K, Tsujimoto, M., and Esko, J. D. (2000) *J Biol Chem*,
2. Habuchi, H., Tanaka, M., Habuchi, O., Yoshida, K., Suzuki, H., Ban, K., and Kimata, K. (2000) *J Biol Chem* 275, 2859-2868
3. Shworak, N. W., Liu, J., Petros, L. M., Zhang, L., Kobayashi, M., Copeland, N. G., Jenkins, N. A., and Rosenberg, R. D. (1999) *J Biol Chem* 274, 5170-5184
4. Bernfield, M., Gotte, M., Park, P. W., Reizes, O., Fitzgerald, M. L., Lincecum, J., and Zako, M. (1999) *Annu Rev Biochem* 68, 729-777
5. Lander, A. D., and Selleck, S. B. (2000) *J Cell Biol* 148, 227-232
6. Lindahl, U. (1999) *Haemostasis* 29 Suppl S1, 38-47
7. Perrimon, N., and Bernfield, M. (2000) *Nature* 404, 725-728
8. Rosenberg, R. D., Shworak, N. W., Liu, J., Schwartz, J. J., and Zhang, L. (1997) *J Clin Invest* 100, S67-75
9. Rostand, K. S., and Esko, J. D. (1997) *Infect Immun* 65, 1-8
10. Selleck, S. B. (2000) *Trends Genet* 16, 206-212
11. Shukla, D., Liu, J., Blaiklock, P., Shworak, N. W., Bai, X., Esko, J. D., Cohen, G. H., Eisenberg, R. J., Rosenberg, R. D., and Spear, P. G. (1999) *Cell* 99, 13-22
12. Atha, D. H., Stephens, A. W., and Rosenberg, R. D. (1984) *Proc Natl Acad Sci USA* 81, 1030-1034
13. Atha, D. H., Lormeau, J. C., Petitou, M., Rosenberg, R. D., and Choay, J. (1985) *Biochemistry* 24, 6723-6729
14. Atha, D. H., Lormeau, J. C., Petitou, M., Rosenberg, R. D., and Choay, J. (1987) *Biochemistry* 26, 6454-6461
15. Lindahl, U., Backstrom, G., and Thunberg, L. (1983) *J Biol Chem* 258, 9826-9830.
16. Lindahl, U., Thunberg, L., Backstrom, G., Riesenfeld, J., Nordling, K., and Bjork, I. (1984) *J Biol Chem* 259, 12368-12376.
17. Shworak, N. W., Liu, J., Fritze, L. M., Schwartz, J. J., Zhang, L., Logeart, D., and Rosenberg, R. D. (1997) *J Biol Chem* 272, 28008-28019
18. Liu, J., Shworak, N. W., Fritze, L. M. S., Edelberg, J. M., and Rosenberg, R. D. (1996) *J Biol Chem* 271, 27072-27082
19. Zhang, L., Schwartz J. J., Miller, J., Liu, J., Fritze, L. M., Shworak, N. W., and Rosenberg, R. D. (1998) *J Biol Chem* 273, 27998-28003
20. Zhang, L., Yoshida, K., Liu, J., and Rosenberg, R. D. (1999) *J Biol Chem* 274, 5681-5691
21. Loganathan, D., Wang, H. M., Mallis, L. M., and Linhardt, R. J. (1990) *Biochemistry* 29, 4362-4368

22. Conrad, H. E. (1998) *Heparin-Binding Proteins*, Academic Press, San Diego
23. Esko, J. D., Weinke, J. L., Taylor, W. H., Ekborg, G., Rodén, L., Anantharamaiah, G., and Gawish, A. (1987) *Journal Of Biological Chemistry* 262, 127189-12195
24. Esko, J. D., Stewart T. E., and Taylor, W. H. (1985) *Proceedings Of The National Academy Of Sciences Of The United States Of America* 82, 3197-3201
25. Esko, J. D., Elgavish, A., Prasthofer, T., Taylor, W. H., and Weinke, J. L. (1986) *Journal Of Biological Chemistry* 261, 15725-15733
26. Bai, X., and Esko, J. D. (1996) *J Biol Chem* 271, 17711-17717
27. Bai, X., Wei, G., Sinha, A., and Esko, J. D. (1999) *J Biol Chem* 274, 13017-13024
28. Wei, G., Bai, X., Gabb, M. M., Bame, K. J., Koshy, T. I., Spear, P. G., and Esko, J. D. (2000) *J Biol Chem* 275, 27733-27740
29. Zhang, L., Lawrence, R., Schwartz, J. J., Bai, X., Wei, G., Esko, J. D., and Rosenberg, R. D. (2001) *J Biol Chem* 276, 28806-28813
30. Dulbecco, R., and Vogt, M. (1954) *J. Exp. Med.* 99, 167-182
31. Esko, J. D. (1989) *Methods Cell Biol* 32, 387-422
32. Habuchi, H., Kobayashi, M., and Kimata, K. (1998) *J Biol Chem* 273, 9208-92113
33. Yamada, S., Yoshida, K., Sugiura, M., Sugahara, K., Khoo, K. H., Morris, H. R., and Dell, A. (1993) *J Biol Chem* 268, 4780-4787.
34. Yamada, S., Murakami, T., Tsuda, H., Yoshida, K., and Sugahara, K. (1995) *J Biol Chem* 270, 8696-8705.
35. Shively, J. E., and Conrad, H. E. (1976) *Biochemistry* 15, 3932-3942
36. Liu, J., Shriver, Z., Blaiklock, P., Yoshida, K., Sasisekharan, R., and Rosenberg, R. D. (1999) *J Biol Chem* 274, 38155-38162
37. Liu, S., Zhou, F., Hook, M., and Carson, D. D. (1997) *Proc Natl Acad Sci USA* 94, 1739-1744.
38. MacRae, I. J., Rose, A. B., and Segel, I. H. (1998) *J Biol Chem* 273, 28583-28589.
39. Zaia, J., and Costello, C. E. (2001) *Anal Chem* 73, 233-239.
40. Jayson, G. C., Lyon, M., Paraskeva, C., Turnbull, S. E., Deakin, J. A., and Gallagher, J. T. (1998) *J Biol Chem* 273, 51-57
41. Lindahl, U., Kusche-Gullberg, M., and Kjellen. L. (1998) *J Biol Chem* 273, 24979-24982
42. Habuchi, H., Habuchi, O., and Kimata, K. (1995) *J Biol Chem* 270, 4172-4179

The invention claimed is:

1. An in vitro method of transferring a sulfate on to the 6-O position of a GlcNAc sugar residue in a polysaccharide preparation, the method comprising the steps of
   (a) providing a polysaccharide preparation having GlcNAc sugar residues, and
   (b) contacting the polysaccharide preparation provided in (a) with glucosaminyl-6-O-sulfotransferase (6-OST) protein in the presence of a sulfate donor whereby the 6-OST protein adds a sulfate to the 6-O-position of a GlcNAc sugar residue; and
   wherein said polysaccharide preparation comprises heparin.

2. The method of claim 1, whereby the polysaccharide preparation comprises glucuronic acid (GlcUA) residues.

3. The method of claim 1, whereby the polysaccharide preparation includes GlcUA-GlcNAc 2 sugar residues.

4. The method of claim 1, whereby the polysaccharide preparation includes disaccharides elected from the consisting of GlcUA/IdoUA-GlcNS, IdoUA2S-GlcNS, and GlcUA-GlcNS3S.

5. The method of claim 1, whereby the polysaccharide preparation includes GlcNAc/NS6S-GlcUA-GlcNS3 S±6S-IdoUA2S-GlcNS6S.

6. The method of claim 1, whereby the polysaccharide preparation includes GlcNAc/NS-GlcUA-GlcNS3 S±6S-IdoUA2S-GlcNS6S.

7. The method of claim 1, whereby the polysaccharide preparation includes GlcNAc/NS6S-GlcUA-GlcNS3S±-IdoUA2S-GlcNS6S.

8. The method of claim 1, whereby the polysaccharide preparation includes GlcNAc/NS6S-GlcUA-GlcNS3S±6S-IdoUA2S-GlcNS.

9. The method of claim 1, whereby the 6-OST protein is a recombinant protein.

10. The method of claim 9, whereby the 6-OST protein is a human recombinant protein.

11. The method of claim 9, whereby the recombinant protein is produced in a expression system selected from the group consisting of baculovirus cells, yeast cells, bacterial cells, and mammalian cells.

12. The method as in claim 1, whereby the sulfate donor is 3'-phospho-adenosine 5'-phosphosulfate (PAPS).

13. The method of claim 1, whereby the 6-O-sulfation is performed in a reaction mixture comprising at least one chloride salt and wherein the pH is between 6.5 and 7.5.

14. The method of claim 1, whereby the polysaccharide preparation is contacted with 6-OST protein in the presence of a sulfate donor for at least 20 minutes.

15. An in vitro method of enriching the portion of anticoagulant active Heparin Sulfate ($HS^{act}$) present in a polysaccharide preparation comprising:
   (a) providing a d-O-sulfated polysaccharide preparation; and
   (b) contacting the preparation with 6-OST protein in the presence of a sulfate donor under conditions, which permit the 6-OST protein to add a sulfate to the 6-O-position of a GlcNAc sugar residue, wherein step (b) occurs concurrent with or subsequent to step (a).

16. The method of claim 15, whereby the 3-O-sulfated polysaccharide preparation is made in a CHO cell that expresses 3-OST-1 protein.

17. The method of claim 16, whereby the 3-O-sulfate polysaccharide preparation is prepared by contacting anticoagulant inactive Heparin Sulfate ($HSin^{act}$) with 3-OST-1 protein.

18. The method of claim 15, whereby the polysaccharide preparation comprises heparan.

19. The method of claim 15, whereby the percentage of $HS^{act}$ present in the polysaccharide preparation following step (b) is greater than 70%.

20. The method of claim 15, whereby the percentage of $HS^{act}$ present in the polysaccharide preparation following step (b) is greater than 50%.

21. The method of claim 15, whereby the polysaccharide preparation comprise N-acetylglucosamine (GlcNAc) and glucuronic acid (GlcUA) residues.

22. The method as in claim 15, whereby the polysaccharide preparation includes sugar residues selected from the group consisting of GlcUA/IdoUA-GlcNS, GlcUA-GlcNAc, IdoUA2S-GlcNS, and GlcUA-GlcNS3S.

23. The method of claim 15, whereby the sulfate donor comprises PAPS.

24. The method of claim 15, whereby the 6-O-sulfation is performed in a reaction mixture comprising at least one chloride salt at a pH of about 6.5-7.5.

25. The method as in any one of claim 24, whereby the 6-OST protein comprises a polypeptide selected from the group consisting of
   (a) human 6-OST-1 (SEQ ID NO. 3);
   (b) human 6-OST-2A (SEQ ID NO. 4);
   (c) human 6-OST-2B (SEQ ID NO. 5);
   (d) human 6-OST-3 (SEQ ID NO. 6).

* * * * *

UNITED STATES PATENT AND TRADEMARK OFFICE
CERTIFICATE OF CORRECTION

PATENT NO. : 8,067,196 B2  
APPLICATION NO. : 10/473180  
DATED : November 29, 2011  
INVENTOR(S) : Robert Rosenberg It is certified that error appears in the above-identified patent and that said Letters Patent is hereby corrected as shown below:

Please delete the paragraph titled 'GOVERNMENT SUPPORT' encompassing column 1, lines 21-24:

"Work described herein was supported by National Institutes of Health Grants 5-P01-HL41484, 5-R01-HL58479, and GM-50573. The Government has certain rights in the invention."

and replace with:

--This invention was made with government support under Grant No. P01 HL041484 awarded by the National Institutes of Health. The government has certain rights in this invention.--

Signed and Sealed this
Thirtieth Day of October, 2012

David J. Kappos
*Director of the United States Patent and Trademark Office*